United States Patent
Woodard, Jr. et al.

(10) Patent No.: US 7,393,343 B2
(45) Date of Patent: Jul. 1, 2008

(54) RETRACTABLE HYPODERMIC SYRINGE

(75) Inventors: James A. Woodard, Jr., Powell, OH (US); Eric G. Hassenpflug, Westerville, OH (US); Steven Huckaby, Columbus, OH (US); Steven R. Nelson, Grove City, OH (US); Eric R. Navin, Delaware, OH (US)

(73) Assignee: Hypoguard USA Inc., Edina, MN (US)

( * ) Notice: Subject to any disclaimer, the term of this patent is extended or adjusted under 35 U.S.C. 154(b) by 825 days.

(21) Appl. No.: 10/190,441

(22) Filed: Jul. 2, 2002

(65) Prior Publication Data
US 2004/0122375 A1 Jun. 24, 2004

(51) Int. Cl.
*A61M 5/32* (2006.01)
(52) U.S. Cl. .................................................... 604/195
(58) Field of Classification Search ................ 604/110, 604/196, 187, 181, 218, 195, 220, 221; 600/432
See application file for complete search history.

(56) References Cited

U.S. PATENT DOCUMENTS

| | | | | |
|---|---|---|---|---|
| 4,957,490 | A | 9/1990 | Byrne et al. | 604/197 |
| 5,211,628 | A | 5/1993 | Marshall | 604/110 |
| 5,484,421 | A | 1/1996 | Smocer | 604/195 |
| 5,693,023 | A | 12/1997 | Adams | 604/195 |
| 5,782,804 | A | 7/1998 | McMahon | 604/110 |
| 5,997,511 | A * | 12/1999 | Curie et al. | 604/195 |
| 6,050,977 | A | 4/2000 | Adams | 604/195 |
| 6,409,701 | B1 | 6/2002 | Cohn et al. | 604/110 |
| 6,676,641 | B2 * | 1/2004 | Woodard et al. | 604/187 |
| 2003/0065287 | A1 * | 4/2003 | Spohn et al. | 604/154 |

FOREIGN PATENT DOCUMENTS

| | | |
|---|---|---|
| WO | WO 01/41843 | 6/2001 |
| WO | WO 02/066097 | 8/2002 |

OTHER PUBLICATIONS

U.S. Appl. No. 10/450,573, filed Jan. 7, 2002 to Field et al.
U.S. Appl. No. 10/247,781, filed Sep. 16, 2002 to Montalvo et al.
U.S. Appl. No. 10/345,901, filed Jan. 16, 2003 to Campbell et al.

* cited by examiner

*Primary Examiner*—Kevin C. Sirmons
*Assistant Examiner*—Catherine N. Witczak
(74) *Attorney, Agent, or Firm*—Connolly Bove Lodge & Hutz LLP

(57) ABSTRACT

A hypodermic syringe includes a barrel with a plunger slidably extending therein. The plunger includes an outer plunger element and an inner plunger element telescoping together. A plunger cap may be advanced after injection to rotate the plunger. A resistance lock retains the cap and plunger indexed until actuation. The rotation actuates latches and locking fingers on the luer hub to engage a probe axially and rotationally on the seal end of the plunger and disengage the slots in the barrel, respectively. The rotation disengages the seal stop to release the annular seal and finally releases the engagement between the outer plunger element and inner plunger element. The foregoing provides for the retraction of the luer hub and associated needle into the barrel.

25 Claims, 22 Drawing Sheets

RETRACTABLE HYPODERMIC SYRINGE

BACKGROUND OF THE INVENTION

The field of the present invention is hypodermic syringes with safety systems for the avoidance of sharps injuries.

For some time the art has recognized the desirability of protecting personnel from accidental sharps injuries, or needle sticks, and against contact with fluid that leaks, drips or is sprayed from a syringe after the syringe is used to deliver an injection. Sometimes, after a syringe is used to inject fluid into a patient, some fluid remains in the syringe, particularly at the tip of the needle. This fluid may include the fluid injected into the patient from the syringe and/or body fluids from the patient such as blood. Any fluid remaining in the syringe after use of the syringe may leave the syringe, such as by leaking, spraying or dripping from the syringe and may contact persons or objects in the area. Syringes with retractable needles may be especially prone to this loss of fluid when the needle quickly retracts into the barrel of the syringe after injection.

More recently, concerns have been expressed about the possibility of transmitting serious or potentially fatal infections as a result of sharps accidents. Most recently, legislation requiring the use of safe needle technology is pending in a number of states and before the Occupation Safety and Health Administration. Safe, conveniently used and inexpensive systems are needed which reduce the amount of manual manipulation required to make the needle safe against sharps injuries and fluid dispersal.

SUMMARY OF THE INVENTION

The present invention is directed to apparatus and methods of operation for hypodermic syringe systems with retractable needles. The syringe includes a barrel and a plunger slidably extending into the barrel with features and steps permitting further manipulation of the plunger following injection to retract a luer hub into the barrel.

In a first separate aspect of the present invention, the retractable syringe includes a cap at one end of the plunger adjacent the opposite end of the barrel from the luer hub. The cap includes an annular body with an inclined slot and a cam driver. The plunger includes a cam surface at the one end of the plunger inclined to the centerline of the bore of the barrel which is engageable with the cam driver. A pin extends substantially radially of the plunger adjacent the one end of the plunger and is engageable with the inclined slot. The cam driver and cam surface are able to provide rigid structure for forced rotation of the plunger relative to the cap. The slot and pin provide for retraction of the plunger from the barrel as well.

In a second separate aspect of the present invention, the first separate aspect may further contemplate a resistance lock extending into the slot. Such a stop might include a rounded bump. This provides a controlled resistance to rotation between the cap and the plunger before the cap can be indexed to the barrel.

In a third separate aspect of the present invention, the retractable syringe includes a cap at one end of the plunger adjacent the opposite end of the barrel from the luer hub. The cap includes an annular body with an inclined slot. The plunger includes a pin extending substantially radially of the plunger adjacent the one end of the plunger and engageable with the inclined slot. A resistance lock extends into the slot. Such a lock might include a rounded bump extending into the inclined slot for a measured resistance profile as the pin moves through the slot. This provides a controlled resistance to rotation between the cap and the plunger before the cap can be indexed to the barrel.

In a fourth separate aspect of the present invention, the third separate aspect may further include an annular body structurally relieved behind the resistance lock. Such relief may be an elongate hole parallel to the inclined slot. The pin may be resiliently mounted for assembly of the cap with the plunger.

In a fifth separate aspect of the present invention, any of the foregoing separate aspects are contemplated to be employed in combination to greater advantage. Further, symmetrical placement of multiple such components as described in the foregoing separate aspects may also be contemplated to center resultant forces. Accordingly, it is an object of the present invention to provide an improved method and apparatus for a needle retracting hypodermic syringe. Other and further objects and advantages will appear hereinafter.

DETAILED DESCRIPTION OF THE PREFERRED EMBODIMENTS

Figure 1:
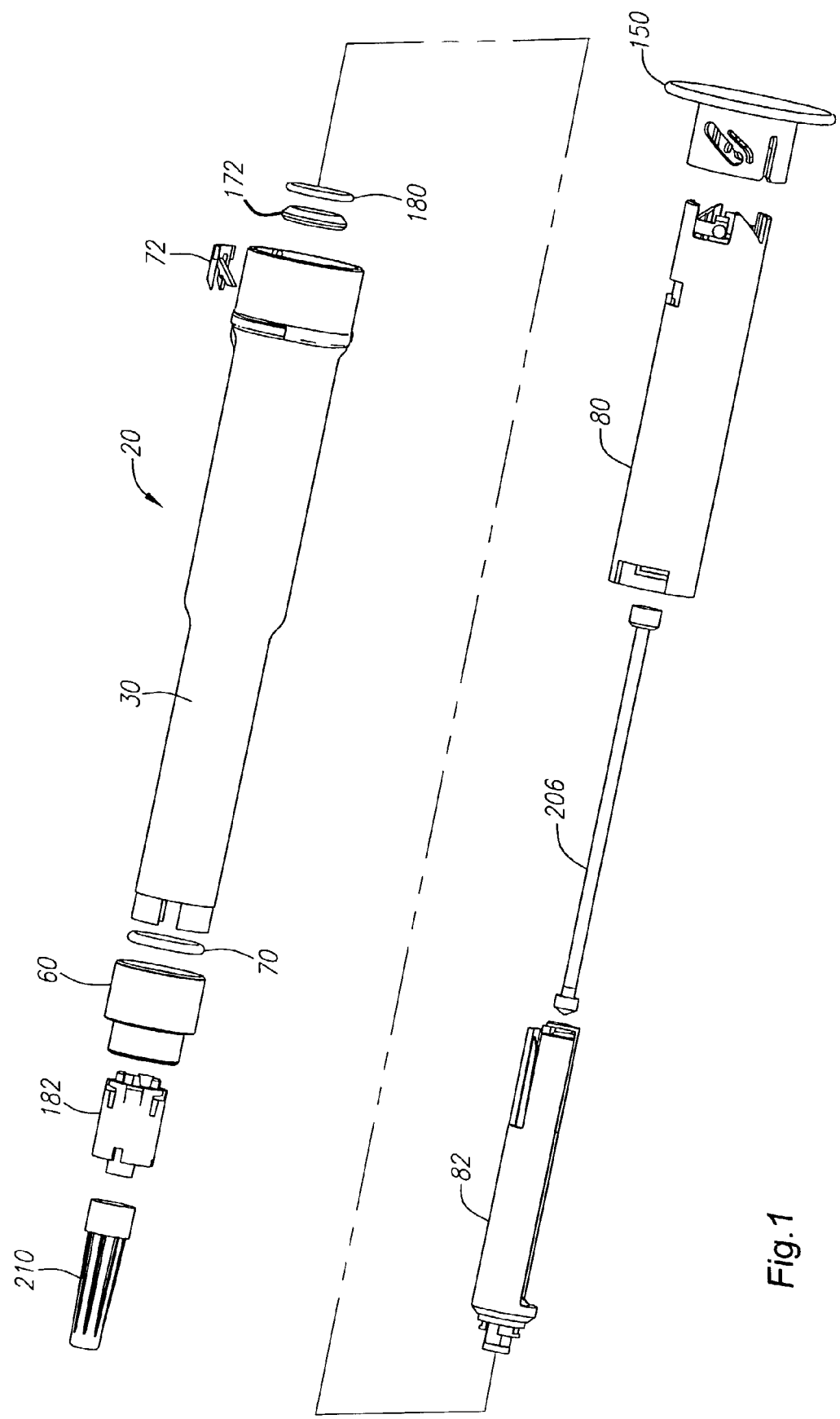
FIG. 1 is an exploded assembly perspective view of a retractable hypodermic syringe.
Figure 2:
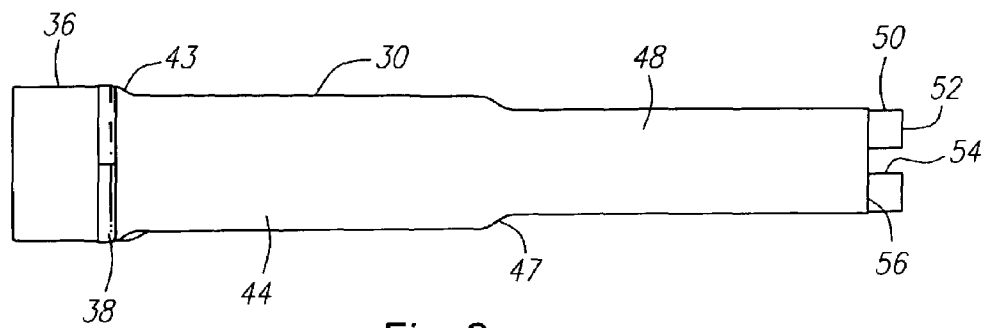
FIG. 2 is a front view of a syringe barrel.
Figure 3:
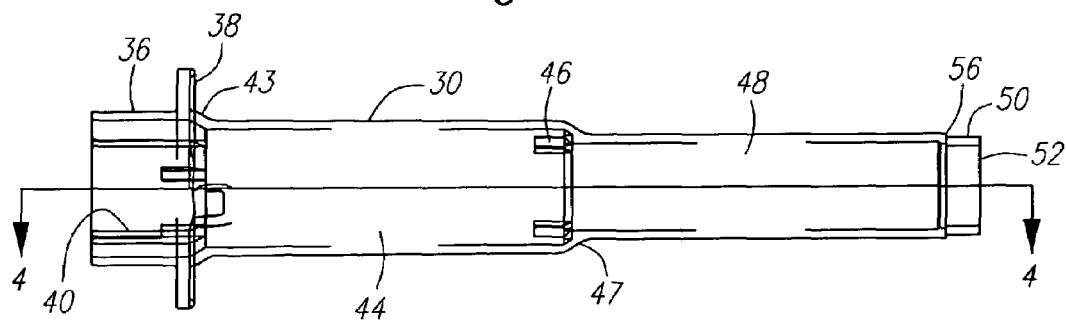
FIG. 3 is a side view of the syringe barrel.
Figure 4:
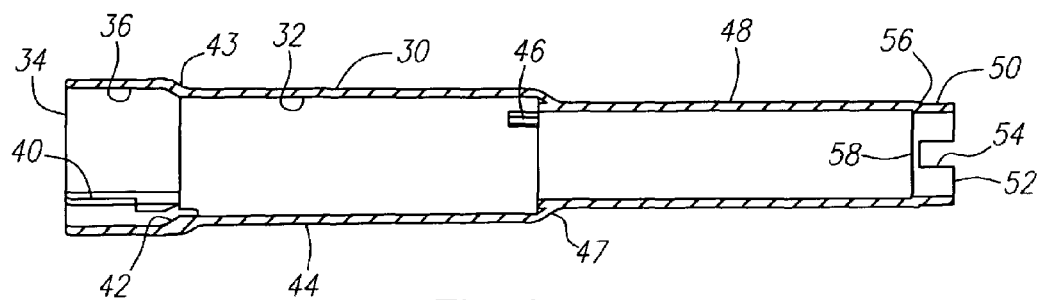
FIG. 4 is a cross-sectional view of the syringe barrel taken along line 4-4 of FIG. 3.
Figure 5:
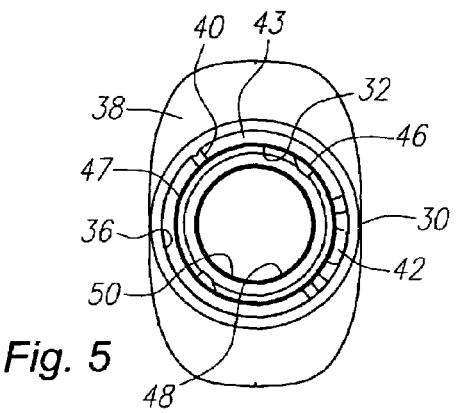
FIG. 5 is an end view of the syringe barrel.

Turning in detail to the figures, a hypodermic syringe, generally designated 20, is shown in an exploded assembly view in FIG. 1. The syringe 20 is retractable in that after injection, the needle may be retracted into the barrel to avoid sharps injuries. The several components depicted in FIG. 1 are described in greater detail with reference to the more detailed figures. Operation of the assembly is also presented.

A barrel 30 is illustrated in FIGS. 2 through 5. The barrel 30 is generally circular in cross section with a bore 32 of varying inside diameters. At the plunger opening 34, the inside diameter is the largest through a first portion 36. A flange 38 extends outwardly from the first portion 36 to define a finger grip. The finger grip 38 may be configured and located to satisfy various ergonomic requirements. Two opposed longitudinal guides 40 extend into the first portion 36 from the plunger opening 34. A snap socket 42 is formed in the wall of the bore 32 to receive a snap, later defined.

The first portion 36 defines an integral truncated conical adapter 43 for transition to a smaller bore. A second portion 44 of the barrel 30 is in axial juxtaposition with the first portion 36. The second portion 44 includes two release elements 46. The release elements 46 are at the far end of the second portion 44 from the first portion 36 and are diametrically opposed to one another. These elements 46 operate to release two elements making up the plunger for plunger contraction as will be described below.

Again, the second portion 44 defines an integral truncated conical adapter 47. A third portion 48 of the barrel 30 is in axial juxtaposition with the second portion 44. This third portion 48 is effectively devoid of detail, forming a simple cylindrical structure. The wall does extend into the second portion 44 as an artifact of manufacturing.

A fourth portion 50 is in axial juxtaposition with the third portion 48. This fourth portion 50 defines the luer end 52 of the barrel 30 and defines two diametrically opposed slots 54 extending substantially from the luer end 52 to the third portion 48. The transition between the third and fourth portions 48, 50 is abrupt, defining a shoulder 56 and internal shoulder 58 as shown at the intersection of the second and third portions 44, 48, which shoulder 58 is not of consequence to the operation of the syringe 20.

A barrel adapter 60 is integrally assembled with the barrel 30 through ultrasonic welding or bonding. The barrel adapter 60 includes a peripheral wall 62 which is cylindrical and extends over the fourth portion 50 of the barrel 30. The peripheral wall 62 abuts against the shoulder 56 and defines an outer boundary for the slots 54. A circular flange 63 extends over the shoulder 56 for receiving excess material at the sonic weld.

Figure 6:
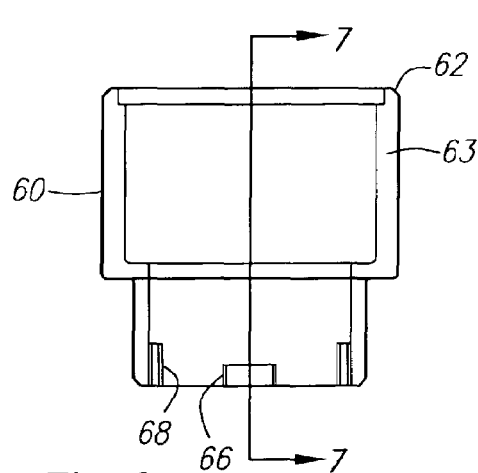
FIG. 6 is a side view of a barrel adapter.
Figure 7:
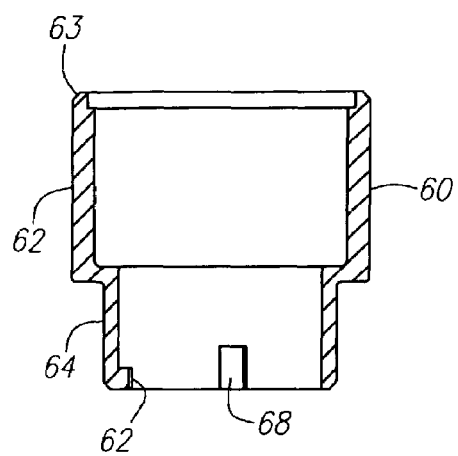
FIG. 7 is a cross-sectional view of the barrel adapter taken along line 7-7 of FIG. 6.
Figure 8:
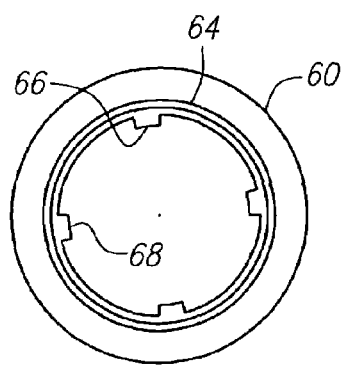
FIG. 8 is a bottom view of the barrel adapter.

The barrel adapter 60 further includes a luer hub socket 64. The socket 64 retains a luer hub described below. The socket includes two sets of inwardly extending pins 66, 68. Each set is diametrically opposed and the two sets differ only in height, with the shorter set avoiding interference with threads on the luer hub. The difference also properly indexes the luer hub relative to the plunger described below. The peripheral wall 62 is longer than the fourth portion 50 of the barrel 30. The area within the peripheral wall 62 between the luer end 52 of the barrel 30 and the luer hub socket 64, when the barrel adapter 60 is assembled with the barrel 30, provides a seat for an annular seal shown in FIG. 1 to be a luer O-ring 70. The barrel adapter 60 is illustrated in detail in FIGS. 6 through 8. The O-ring may alternatively be positioned within an annular groove in the sidewall of the luer hub.

Figure 9:
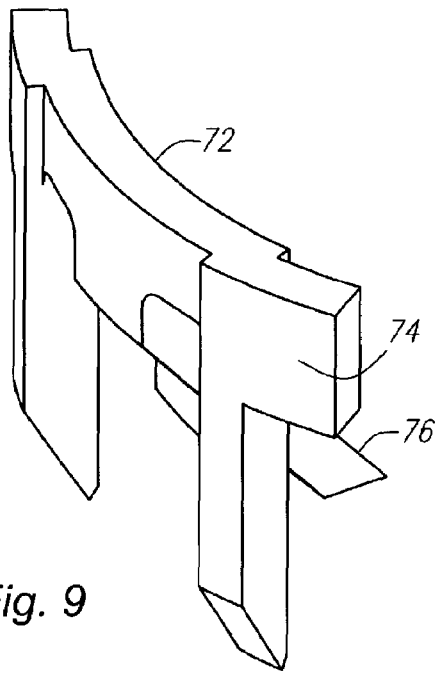
FIG. 9 is a perspective view of a snap.
Figure 10:
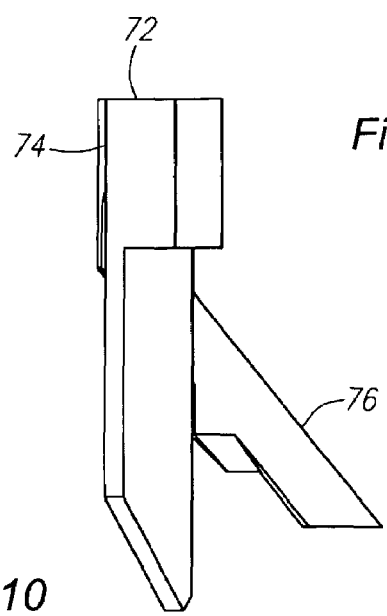
FIG. 10 is a side view of the snap.
Figure 11:
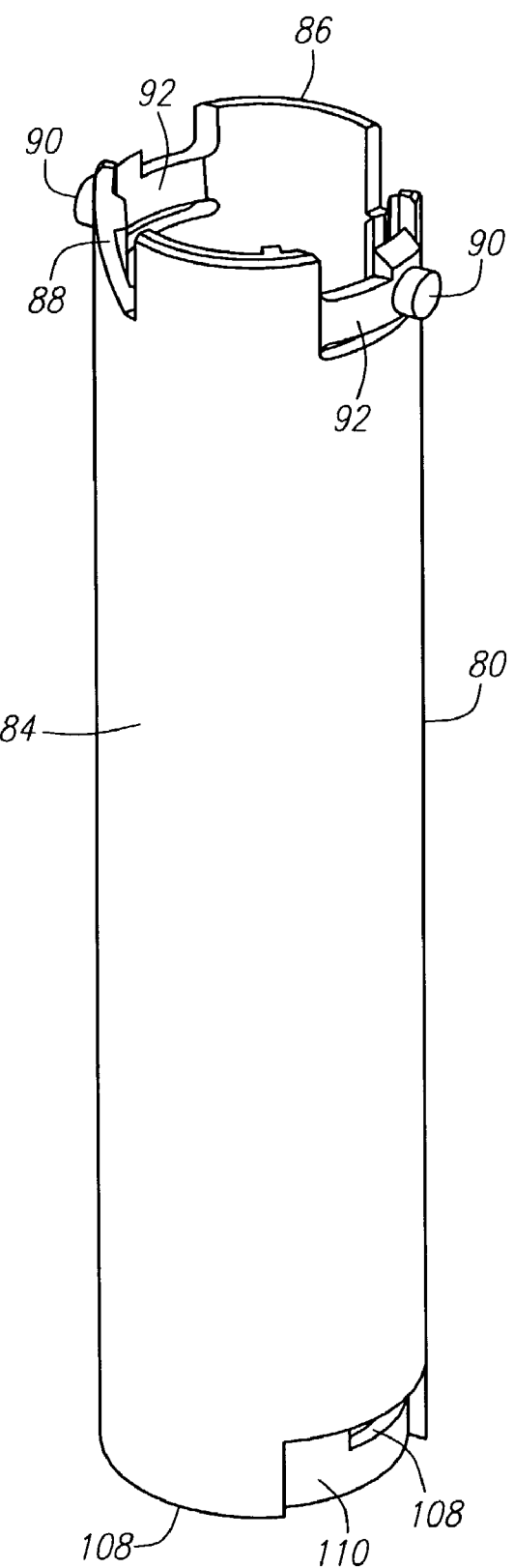
FIG. 11 is a perspective view of an outer plunger element.
Figure 12:
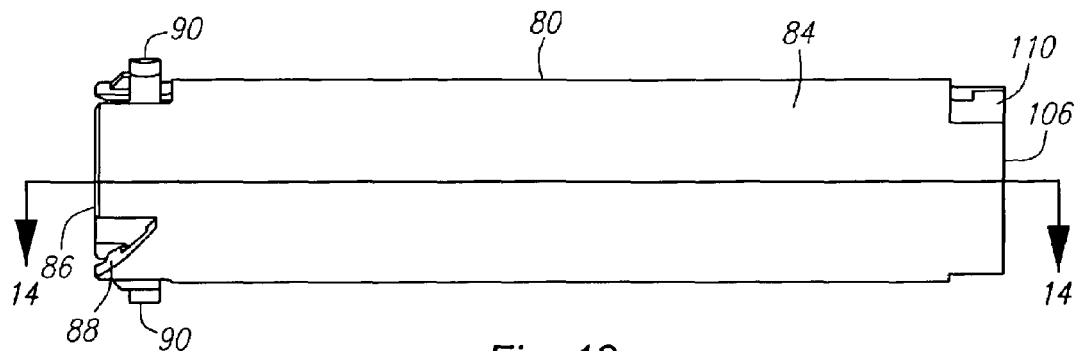
FIG. 12 is a first side view of the outer plunger element.
Figure 13:
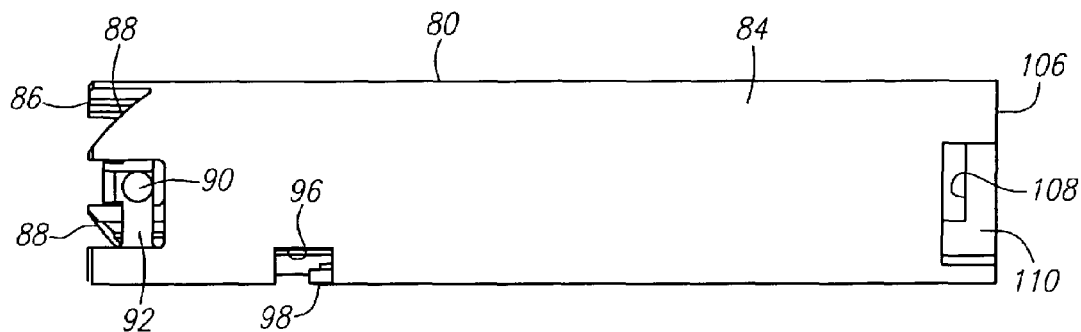
FIG. 13 is a second side view of the outer plunger element.
Figure 14:
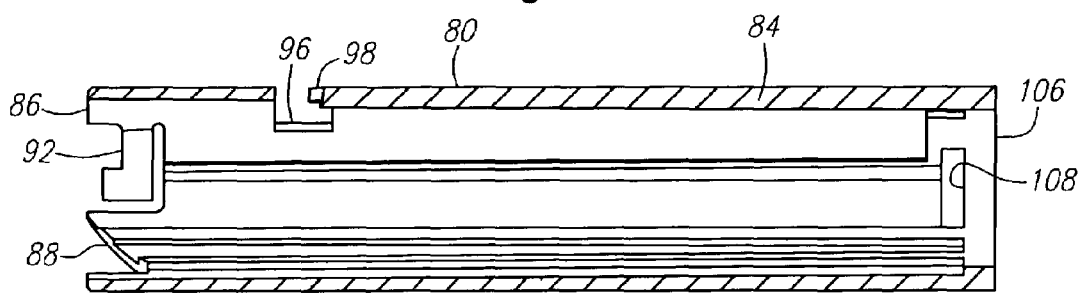
FIG. 14 is a third side view of the outer plunger element.
Figure 15:
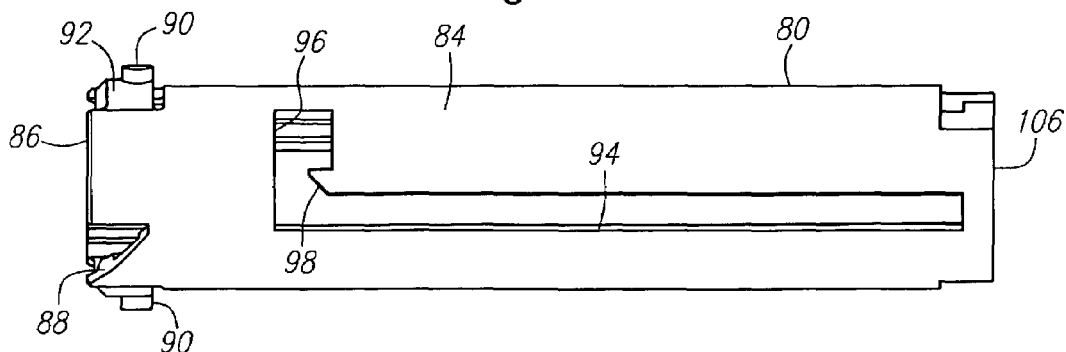
FIG. 15 is a cross-sectional view of the outer plunger element taken along line 15-15 of FIG. 14.
Figure 16:
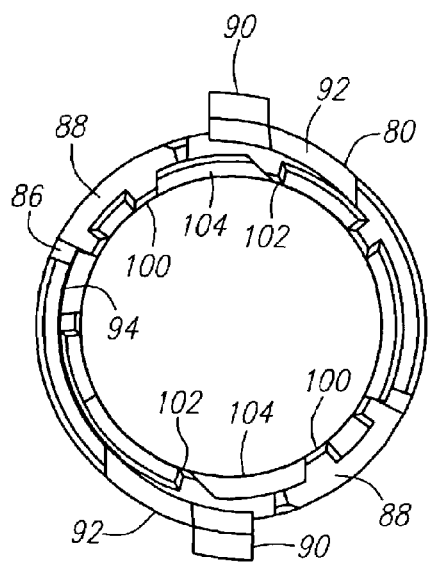
FIG. 16 is an top view of the outer plunger element.
Figure 17:
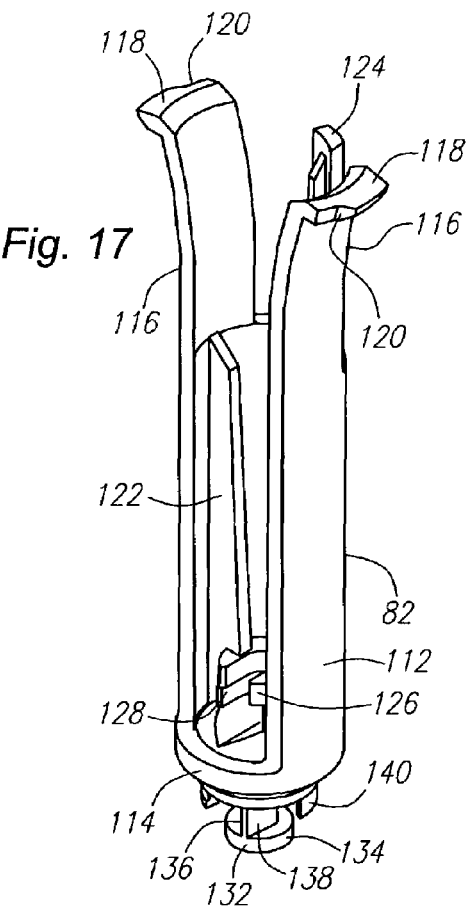
FIG. 17 is a perspective view of an inner plunger element.
Figure 18:
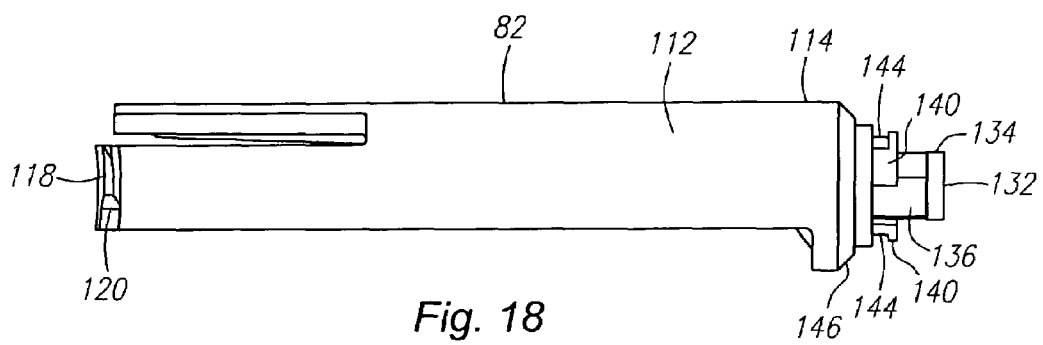
FIG. 18 is a first side view of the inner plunger element.
Figure 19:
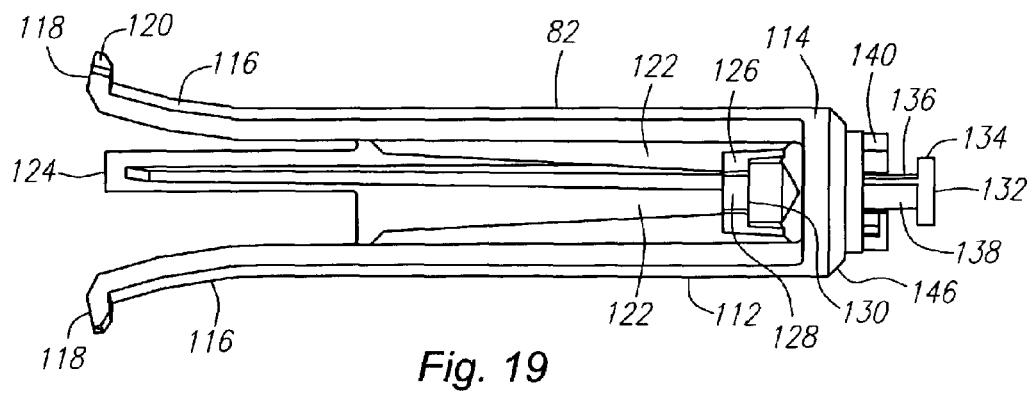
FIG. 19 is a second side view of the inner plunger element.
Figure 20:
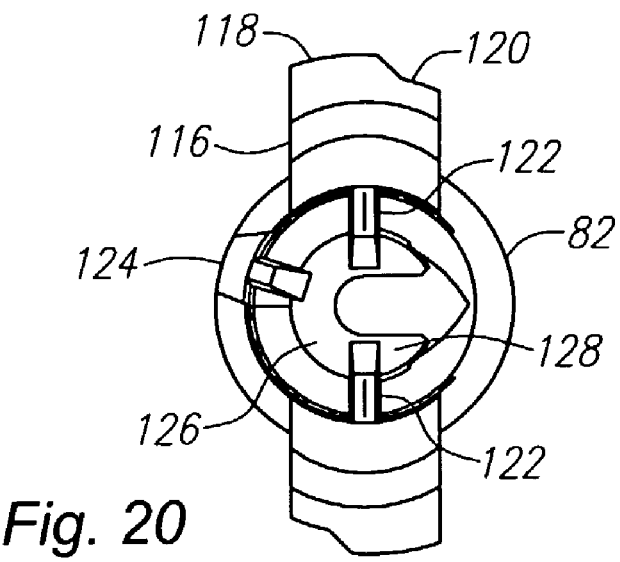
FIG. 20 is a top view of the inner plunger element.
Figure 21:
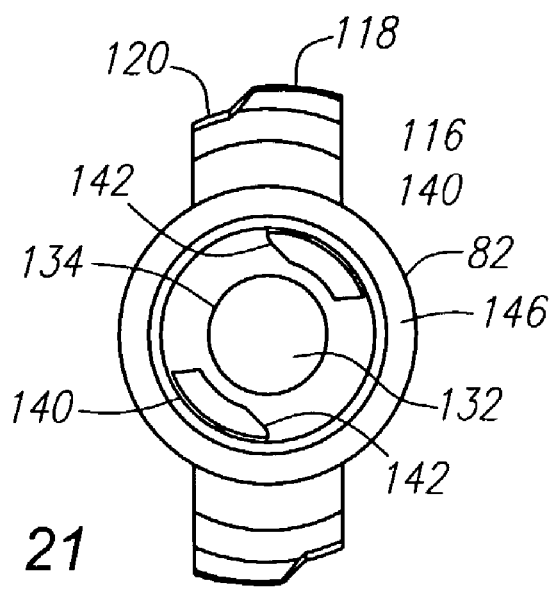
FIG. 21 is a bottom view of the inner plunger element.
Figure 22:
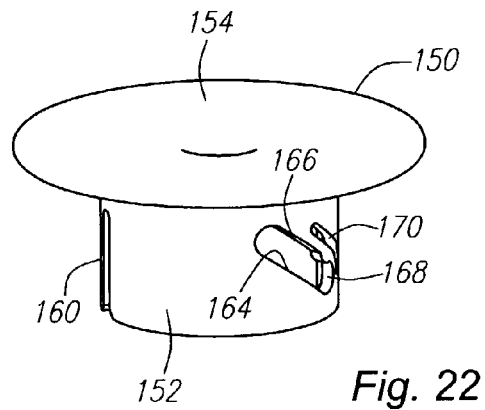
FIG. 22 is a perspective view of a plunger cap.
Figure 23:
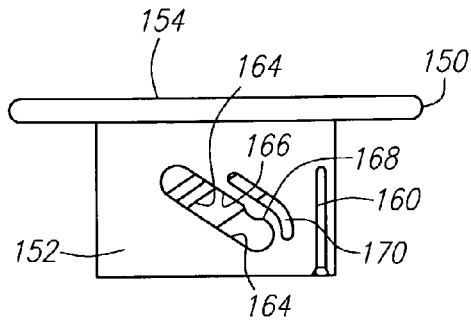
FIG. 23 is a side view of the plunger cap.
Figure 24:
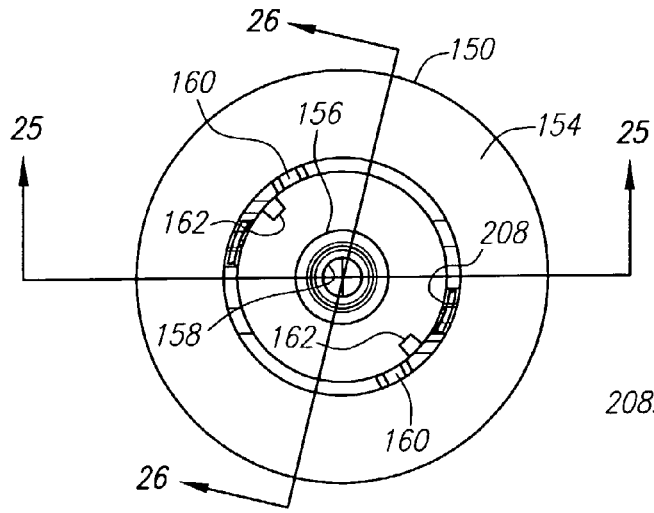
FIG. 24 is a bottom view of the plunger cap.
Figure 25:
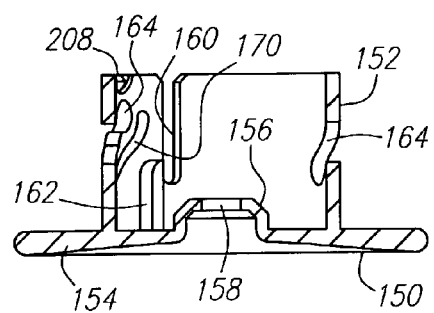
FIG. 25 is a cross-sectional view of the plunger cap taken along line 25-25 of FIG. 24.
Figure 26:
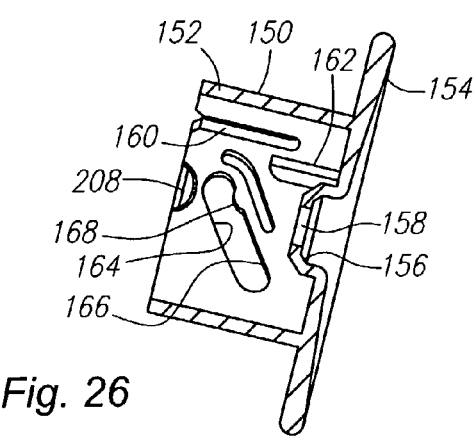
FIG. 26 is a cross-sectional view of the plunger cap taken along line 26-26 of FIG. 24.

A snap 72 includes a curved outer surface 74 to fit within the snap socket 42 where it is bonded in place. The snap includes a resilient finger 76 extending at an angle toward the luer end 52. The resilient finger 76 will bend out to receive the plunger during assembly but resists extraction thereof as will be described below. The snap 72 is illustrated in detail in FIGS. 9 and 10.

A plunger slidably extends into the bore 32 of the barrel 30. This plunger is an assembly including a hollow outer plunger element 80 and hollow inner plunger element 82. These elements 80, 82 are telescoped together. The outer plunger element 80 is illustrated in detail in FIGS. 11 through 16. The inner plunger element 82 is illustrated in detail in FIGS. 17 through 21.

The hollow outer plunger element 80 has a generally cylindrically body 84. The cap end 86 of the hollow outer plunger element 80 extends outwardly of the plunger opening 34 in the barrel 30 when the device is assembled. This cap end 86 includes two cam surfaces 88 diametrically opposed on the rim of the outer plunger element 80. These cam surfaces 88 are inclined to the center line of the cylindrical body 84.

The cap end 86 also includes two diametrically opposed cylindrical pins 90 which are resiliently mounted to the body 84 of the outer plunger element 80 through circumferentially extending arms 92. The pins extend radially outwardly. The resilient mounting through the arms 92 facilitate assembly, allowing radial movement of the pins 90. The pins 90 are otherwise rigid in their orientation relative to the body 84 to which they are attached.

A longitudinal indexing slot 94 extends longitudinally along the body 84 and further includes a circumferential section 96. This section 96 has a locking tooth 98 on one side of the slot 94. This tooth 98 cooperates with a bump on the cap. The tooth 98 has a back shoulder perpendicular to the circumferential section 96, preventing extraction of the snap, once captured therein.

Two sets of longitudinally arranged ribs 100, 102 are found on the bore of the body 84. The ribs of each pair are diametrically opposed and the ribs 100 are arranged adjacent to the ribs 102, respectively, to define guideways 104 which cooperate with the hollow inner plunger element 82. Additional ribs provide strength to the body 84 of the hollow outer plunger element 80 and some axial alignment for the hollow inner plunger element 82. Instead of ribs, the areas not forming the guideways 104 may simply be thick to provide appropriate strength.

Adjacent the engagement end 106 of the hollow outer plunger element 80, opposed sockets 108 extend through the wall of the body 84. The outer wall of the body 84 includes insets 110 about the opposed sockets 108. The surfaces of the insets 110 are substantially aligned with or radially inwardly of the surface of the guideways 104 found on the inner side of the body 84. The sockets 108 are also offset to one side of the insets 110.

The hollow inner plunger element 82 includes a partially cylindrical section 112 terminating in a circular hub 114 at the seal end of the inner plunger element 82. Two opposed longitudinally extending and outwardly splayed arms 116 extend from one end of the cylindrical section 112 away from the circular hub 114. These arms 116 include latches 118 extending from the ends of the arms 116 radially outwardly. The latches 118 each have a beveled side 120 defining a cam follower for cooperation with the release element 46 of the barrel 30. The latches 118 cooperate with the opposed sockets 108 to lock the hollow outer plunger element 80 and the inner plunger element 82 in an extended telescoped arrangement. The arms 116 are splayed outwardly to ensure that plastic creep will not render the latches useless through prolonged storage. Webs 122 also contribute to the strength of the arms 116.

A guide arm 124 is arranged between the arms 116. It also extends longitudinally from the cylindrical section 112. This guide arm 124 is aligned with the longitudinal indexing slot 94 which allows the snap 72 to interfere with extraction of the arm 124 and in turn the entire plunger assembly. The guide arm 124 does not need to extend into the slot. The quadrant of the cylindrical section 112 opposed to the guide arm 124 is open to provide access into the center of the inner plunger element 82.

An attachment 126 is located on the inner side of the circular hub 114. The attachment 126 faces the attachment end of the inner plunger element 82. A slot 128 is presented in the attachment 126 with an under cut cavity 130 behind the slot 128. The neck of a bungee anchor is able to slide into the slot 128 while the head is received in the cavity 130.

The seal end of the circular hub 114 includes a probe 132. The probe includes a generally cylindrical head 134 and an under cut shaft 136. The under cut shaft creates two diametrically positioned flat surfaces 138 on the probe 132. The circular hub 114 also includes diametrically positioned cams 140 having cam surfaces 142 facing inwardly toward the probe 132 but displaced outwardly therefrom. The cams 140 extend axially of the circular hub 114 to define the cam surfaces 142. Additionally, under cut locking grooves 144 are found on the radially outward sides of the cams 140. Finally, the surface of the circular hub 114 about the probe 132 and cams 140 includes an annular truncated conical surface 146.

A plunger cap 150 is illustrated in detail in FIGS. 22 through 26. The cap 150 as shown in FIG. 1 is to be positionable on the cap end 86 of the outer plunger element 80. The cap 150 includes an annular body 152 and a thumb button 154 extending across one end of the annular body 152. The thumb button 154 defines an attachment 156 centered axially of the annular body 152 with a hole 158 to receive a bungee anchor head.

The annular body 152 includes two longitudinal slots 160 diametrically positioned and extending to the free end of the annular body 152. These slots engage the longitudinal guides 40 in the first portion 36 of the barrel 30. This engagement only occurs once the plunger is advanced substantially fully into the barrel 30.

The annular body 152 further includes cam drivers 162 diametrically placed on the inner surface of the annular body 152. These cam drivers engage the cam surfaces 88 on the cap end of the outer plunger 80 with the cap 150 in place on the plunger.

Inclined slots 164 are also diametrically positioned on the annular body 152 and extend therethrough. The inclined slots are sized to receive the radially resiliently mounted cylindrically pins 90 on the outer plunger 80. One side 166 of each of the inclined slots 164, which faces toward the barrel 130 when the plunger is positioned in the barrel, includes a resistance lock 168. The components of the syringe, with the exception of the needle, are preferably of a polymeric material. Consequently, the material is able to flex in appropriate configurations. The resistance lock 168 is a rounded bump and is structurally relieved behind the rounded bump by an elongated relief hole. The cylindrical pins 90 of the plunger are too wide to pass along the inclined slots 164 past the resistance locks 168 without defamation of the rounded bumps into the elongated relief holes 170.

Figure 27:
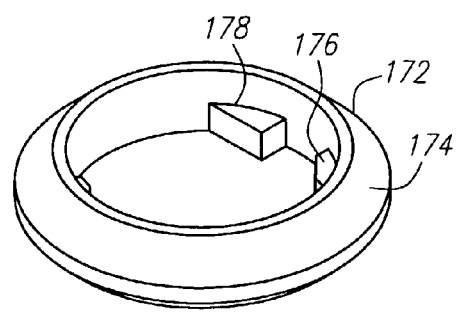
FIG. 27 is a perspective view of a seal stop illustrating the top.
Figure 28:
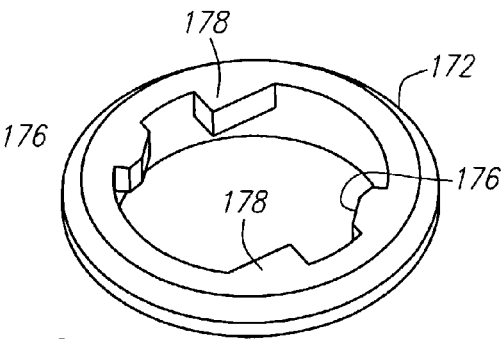
FIG. 28 is a perspective view of the seal stop illustrating the bottom.
Figure 29:
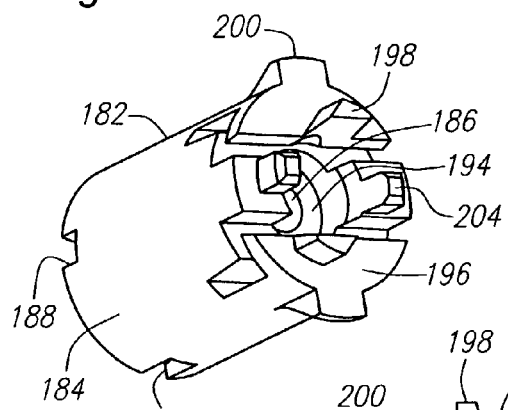
FIG. 29 is a perspective view of a luer hub.
Figure 30:
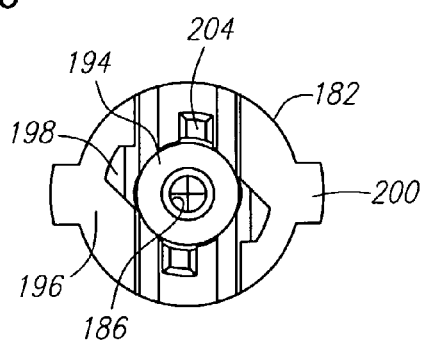
FIG. 30 is a top view of the luer hub.
Figure 31:
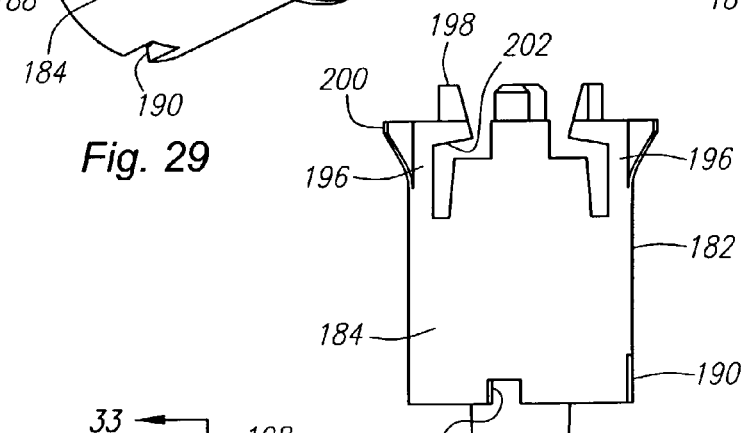
FIG. 31 is a first side view of the luer hub.
Figure 32:
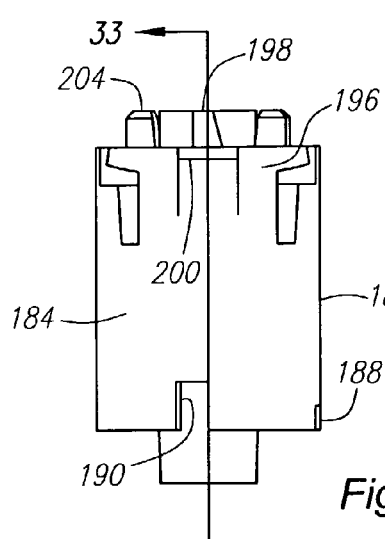
FIG. 32 is a second side view of the luer hub.
Figure 33:
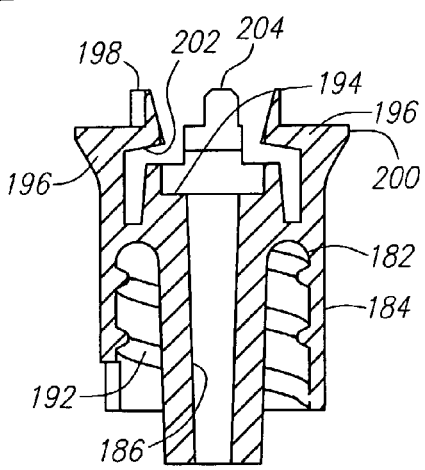
FIG. 33 is a cross-sectional view of the luer hub taken along line 33-33 of FIG. 32.

A seal stop 172 is mounted to the leading side of the circular hub 114 of the plunger. The seal stop 172 is releasable from the circular hub 114 with rotation of the stop 172 relative to the hub 114. The seal stop 172 includes an annular truncated conical surface 174 which cooperates with the surface 146 of the circular hub 114 to define an annular pinch. The seal stop 172 forms a ring with an inner cylindrical surface positionable about the cams 140 on the circular hub 114. Two inwardly extending mounting lugs 176 are retained by the under cut locking grooves 144. Stops 178 are appropriately spaced angularly from mounting lugs 176. The conical surfaces 174 and 146 defining the pinch are able to receive an annular plunger seal 180 in radial expansion within the pinch. The mechanism is sized to force the seal 180 outwardly to seal with the third portion 48 of the barrel 30. The seal stop 172 is illustrated in detail in FIGS. 27 and 28.

A luer hub 182 is illustrated in detail in FIGS. 29 through 33. The luer hub 182 is located in the luer hub socket 64 of the barrel adapter 60 and is axially and rotationally fixed but can be released to axially slide in the barrel 30 from the luer end 52 of the barrel 30 toward the plunger opening 34. The hub 182 includes a generally cylindrical body 184 having a passage 186 extending axially therethrough. Notches 188, 190 receive the pins 66, 68 which both prevent the luer hub 182 from rotating within the barrel adapter 60 and moving axially from the luer end of the syringe. Internal threads 192 meet ISO-594-2 for attachment and removal of a needle assembly thereto.

The engagement end of the luer hub 182 includes a concentrically arranged recess 194 facing the plunger. The recess is arranged and positioned to accept the cylindrical head 134 of the probe 132. The probe 132 engages the luer hub 182 with the cylindrical head 134 contacting the recess 194. At this point, the plunger is substantially fully extended into the barrel 30. Two elements 196 are diametrically placed about the recess 194 on the end of the luer hub 182. These elements are resiliently mounted to the luer hub 182 to move radially. The elements 196 each include a cam follower 198 which extends toward the plunger for engagement with the cam surfaces 142. Locking fingers 200 are also mounted to the elements 196 and extend radially outwardly to releasably, axially engage the slots 54 of the barrel 30. Latches 202 extend radially toward and above the recess 194 to angularly and axially engage the probe 132 by extending into the under cut shaft 136 to the flat surfaces 138. Engagements 204 extend upwardly from the luer hub 182 toward the plunger. These engagements 204 extend to the seal stop 172 to interfere with rotation of the stops 178.

For assembly, the luer O-ring 70 is arranged about the luer hub 182 and the luer hub is positioned within the barrel adapter 60. The barrel adapter 60 is then sonically welded to the barrel 30 with the axial alignment of the luer hub 182 carefully controlled relative to the features on the barrel 30.

The plunger is assembled by locking the seal stop 172 to the under cut locking grooves 144 in the cams 140 of the circular hub 114. The arms 116 are pressed toward one another and the inner plunger element 82 is inserted into the outer plunger element 80.

A resilient tension element 206 is associated with the cap 150, either through molding or physical insertion. The cap is placed on the outer plunger element 80 at the cap end 86. This causes the resilient tension element 206, which is typically a bungee, to extend down into the hollow inner plunger element 82. The tension element 206 has a bungee anchor head at each end with a constricted neck.

Small locating grooves 208 on the inner side of the annular body 152 receive the resiliently mounted cylindrical pins 90. The pins 90 are further compressed and the cap 150 is advanced onto the top end 86 of the outer plunger element 80. The pins 90 become arranged in the inclined slots 164 against the resistance locks 168.

The resilient tension element 206 is tensioned and engaged with the attachment 146 with the inner plunger element 82 slightly telescoped out of the outer plunger element 80. The plunger may then be allowed to again telescope together such that resilient tension element 206 is just substantially relaxed.

The snap 72 is bonded into the barrel 30 in the snap socket 42. The plunger is then introduced into the barrel 30 through the plunger opening 34. The snap 72 is aligned with the longitudinal indexing slot 94 even with the outer plunger element 80 and the inner plunger element 82 telescoped together, the longitudinal indexing slot 94 has sufficient length to accommodate the snap 72.

A needle assembly may be or has been attached to the internal threads 192 of the luer hub 182 and a cap 210 is placed over the needle. In this initial assembly for packaging and storage, the plunger is contracted and advanced substantially fully into the barrel 30.

For use, the cap 150 is gripped along with the barrel 30 and the cap 150 and outer plunger element 80 are drawn from the barrel 30. The snap 72 interferes with movement of the guide arm 124 riding in the longitudinal indexing slot 94 such that the plunger elements 80, 82 are telescoped to an expanded position. This tensions the resilient tension element 206 and ultimately results in the latches 118 of the arms 116 snapping into the opposed sockets 108 such that the plunger is substantially fully extended.

With the syringe thus cocked, the plunger is advanced within the barrel with substantially full extension toward the luer end of the barrel. The cap 150 is not forced into actuating compression toward the barrel at this point.

The cap 210 is removed and the needle is injected into a bottle of fluid to be hypodermically injected into a patient. The plunger is then drawn back for the proper dosage. The injection is accomplished in a normal manner and the needle removed from the subject receiving the injection.

Once the plunger is again substantially fully inserted into the barrel, the cap 150 is forced toward the barrel 30. At this point, the snap 72 is aligned with the circumferential section 96 of the longitudinal indexing slot 94 such that the plunger can now rotate within the barrel 30. The longitudinal slots 160 of the cap 150 are engaged with the longitudinal guides 40 of the barrel 30. Consequently, the cap cannot rotate. Under this circumstance, further application of pressure to the thumb button 154 of the cap 150 will cause the cam drivers 162 to engage the cam surfaces 88 of the outer plunger element 80. Further, the inclined slots 164 which retained the outer plunger element 80 to move with the cap 150 also engage the pins 90. The resistance locks 168 are overcome and the two plunger elements 80, 82 are rotated by the cam drivers 162 and the pins 90 against the incline surfaces.

At the point that the cap 150 is able to initiate rotation of the plunger, the cylindrical head 134 of the probe 130 is located in the recess 194 with the contact preventing additional advancement of the plunger within the barrel 30. As the plunger rotates, the probe 132, the cams 140 and the seal stop 172 rotate. The cam surfaces 142 are oriented to move the cam followers 198 inwardly. Therefore, as the plunger rotates, the cams 140 move the locking fingers 200 and the latches 202 inwardly. The pins 66, 68 retain the luer hub 182 from rotating under the influence of the cams 140. The locking fingers are drawn in this way from the slots 54. The latches 202 extend to engage the cylindrical head 134 of the probe 132 by extending into the under cut shaft 136. With this motion, the luer hub is released from moving axially and is engaged with the plunger.

The engagements 204 simultaneously interfere with the rotation of the seal stop 172 by contacting the stops 178. As the plunger continues to rotate, the mounting lugs 176 are rotated from engagement with the under cut locking grooves 144 on the cams 140. Once unlocked, the annular plunger seal 180 is released to contract away from the barrel 30. Thus, the seal does not generate resistance against motion of the inner plunger element 82.

With the annular plunger seal 180 released, the luer hub 182 capturing the probe 132 and the locking fingers 200 released from the slots 54 of the barrel 30, the needle assembly is prepared to be retracted. Under the influence of the cap 150, continued rotation of the plunger brings the latches 118 into engagement with the release elements 46 in the bore 32 of the barrel 30. The latches 118 are driven inwardly until they release from the opposed sockets 108. The tension element 206 then is able to draw the inner plunger element 82 along with the luer hub 182 upwardly into the barrel 30. As the tension element 206 is at its most stressed with the luer hub still in the socket 64, the luer hub 182 can be drawn through the inner O-ring 70 without the need to relieve it from tension about the luer hub 182.

To achieve release of the latches 118, the snap 72 must pass along the circumferential section 96. The locking tooth 98 is also placed in the circumferential section 96 to interfere with movement relative to the snap 72. This provides additional resistance and tends to keep the plunger rotated once it has been positioned past the locking tooth 98. In this position, the snap 72 prevents extraction of the outer plunger element 80.

The cylindrical head 134 on the probe 132 is arranged such that it is displaced from the latches 202 with the probe 132 fully seated in the recess 194. As the luer O-ring 70 remains about the luer hub 182 as the plunger begins to retract, the plunger will first start to draw a vacuum between the circular hub 114 and the luer hub 182 prior to the cylindrical head 134 engaging the latches 202. This increase in volume behind the luer hub 182 draws liquid from the needle assembly to avoid splash as the needle is then withdrawn.

Figure 34:
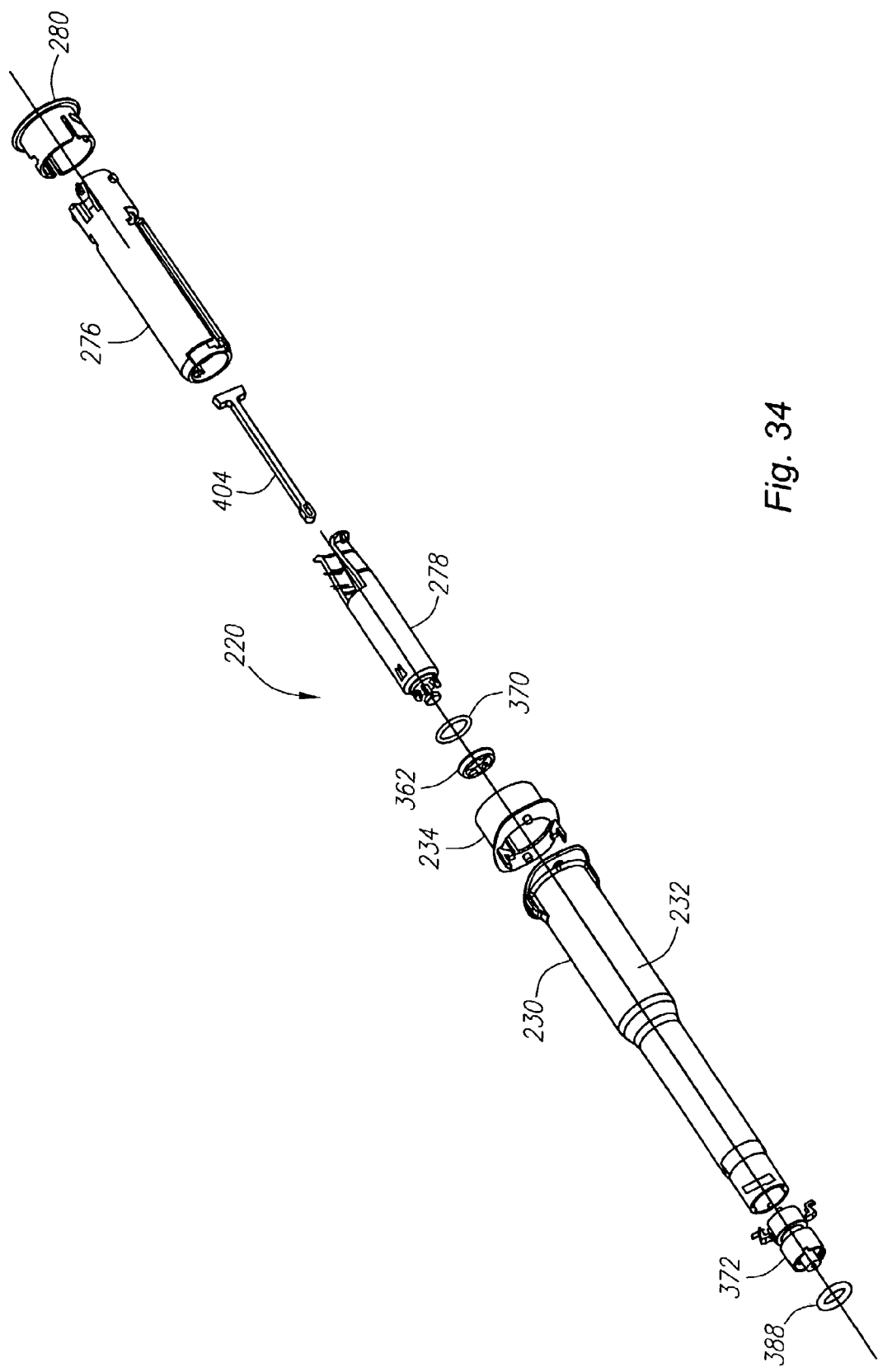
FIG. 34 is an exploded assembly perspective view of a second retractable hypodermic syringe.
Figure 37:
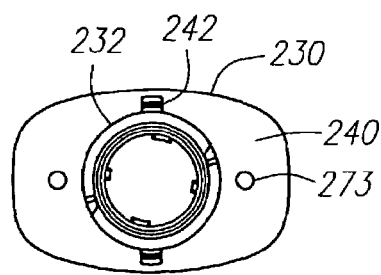
FIG. 37 is a top view of the main body of FIG. 35.
Figures 35, 36:
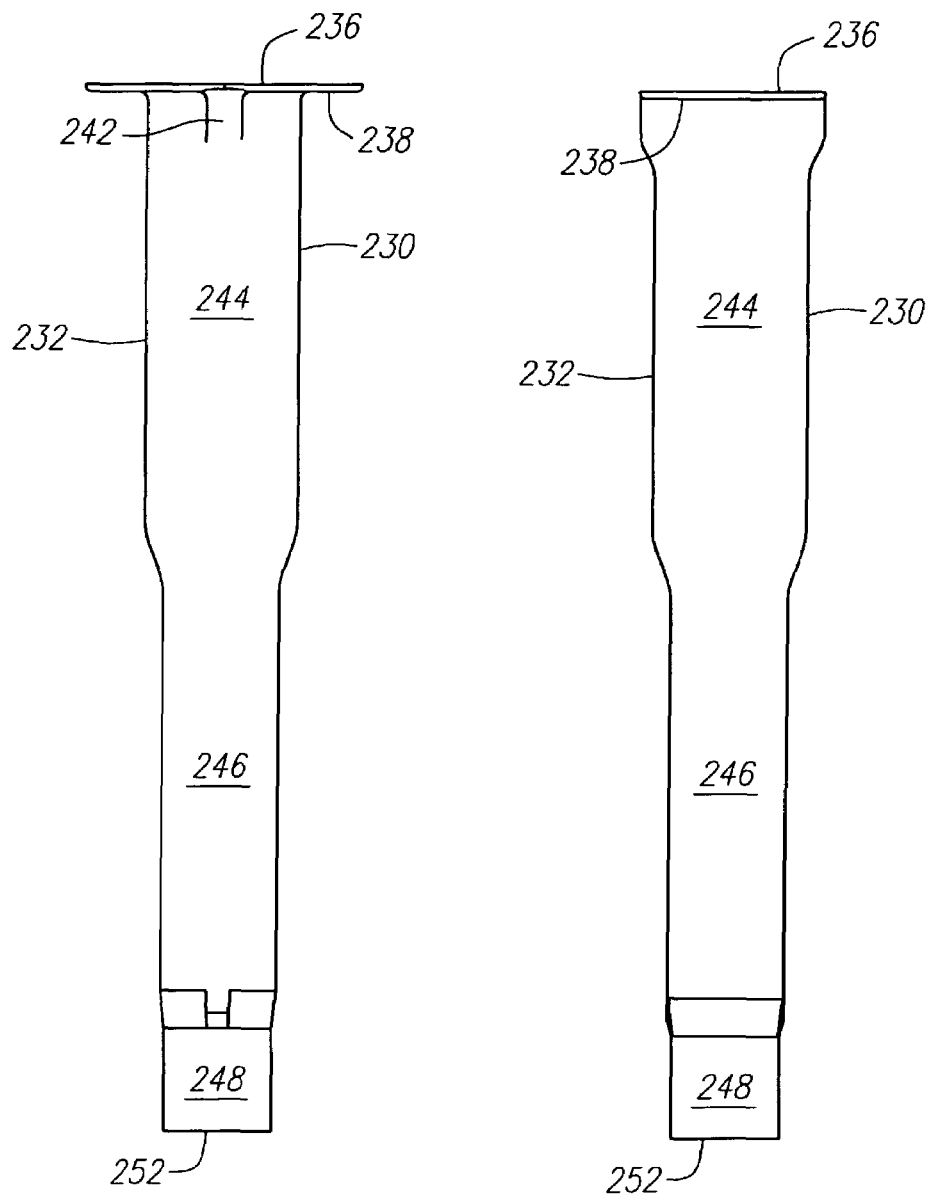
FIG. 35 is a front view of the main body of a syringe barrel of the retractable hypodermic syringe of FIG. 34.
FIG. 36 is a side view of the main body of FIG. 35.
Figure 38:
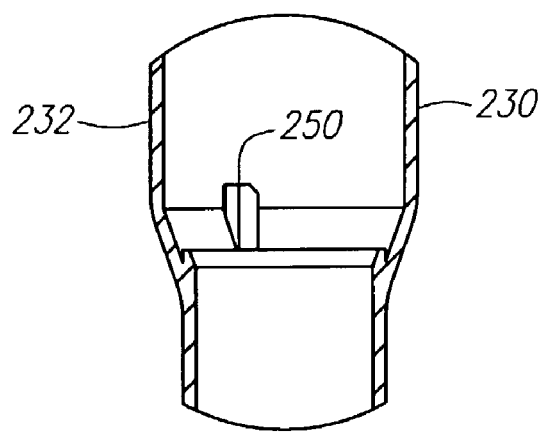
FIG. 38 is a detail cross section of the main body of FIG. 35.
Figure 39:
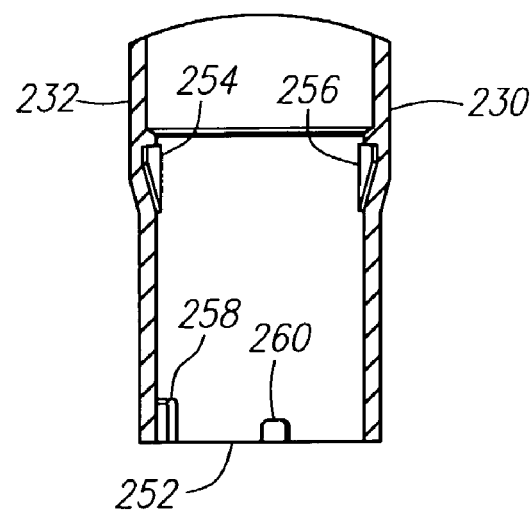
FIG. 39 is a detail cross section of the main body of FIG. 35.
Figure 40:
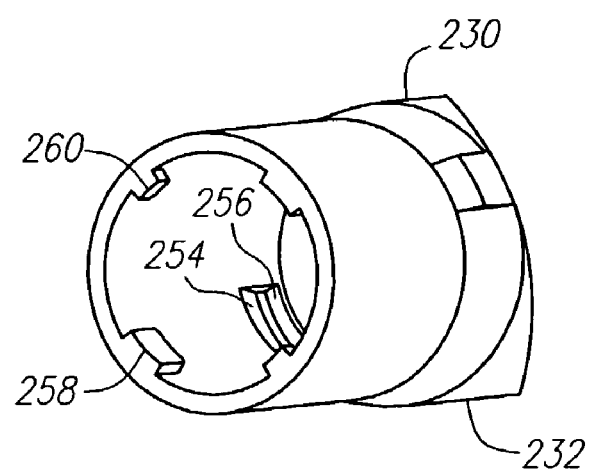
FIG. 40 is a perspective end view of the main body of FIG. 35.
Figure 41:
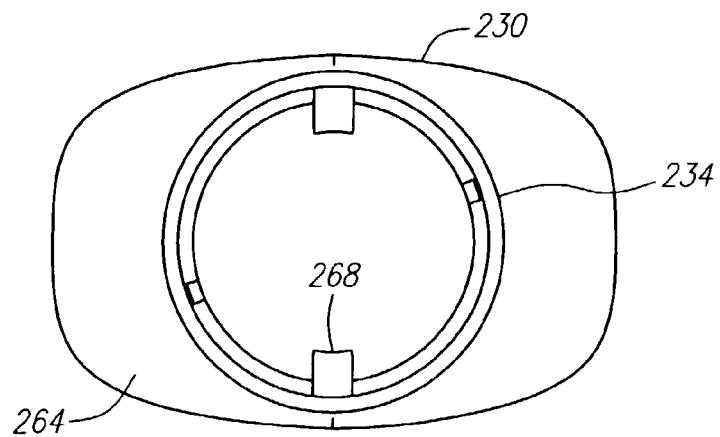
FIG. 41 is a top view of an entry portion of the barrel of the hypodermic syringe of FIG. 34.
Figure 42:
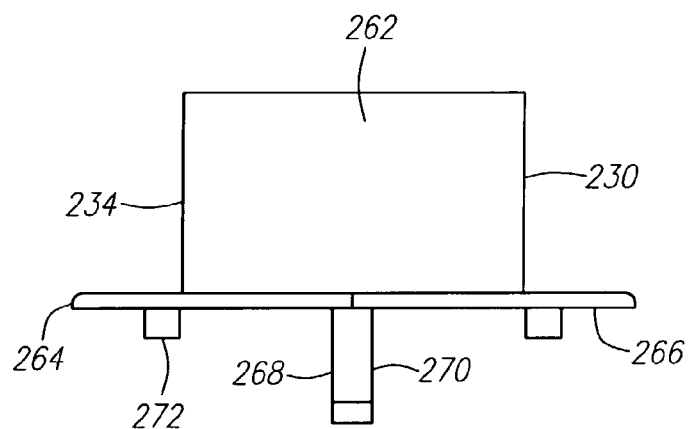
FIG. 42 is a front view of the entry portion of FIG. 41.
Figure 43:
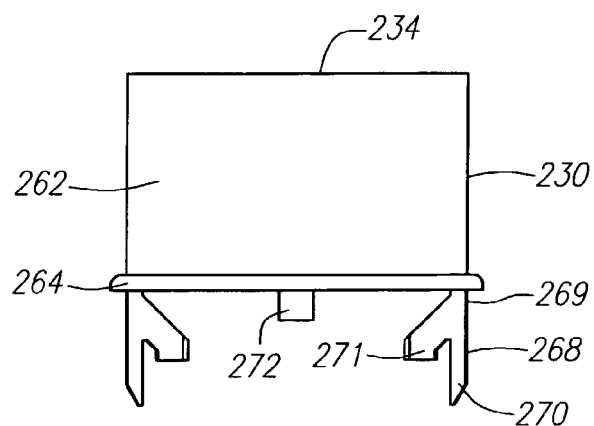
FIG. 43 is a side view of the entry portion of FIG. 41.
Figure 44:
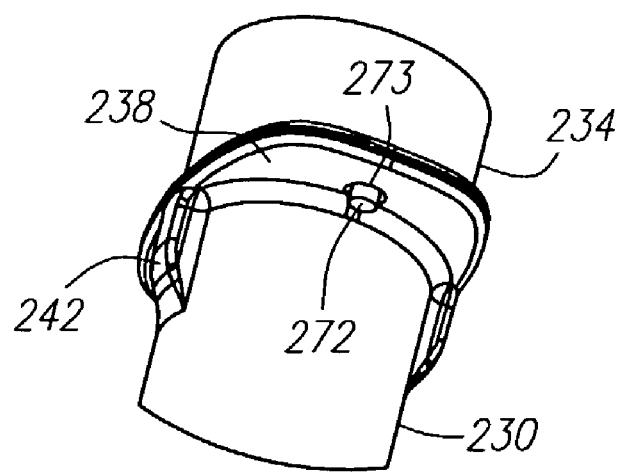
FIG. 44 is a perspective end view of the end portion of FIG. 41.
Figure 45:
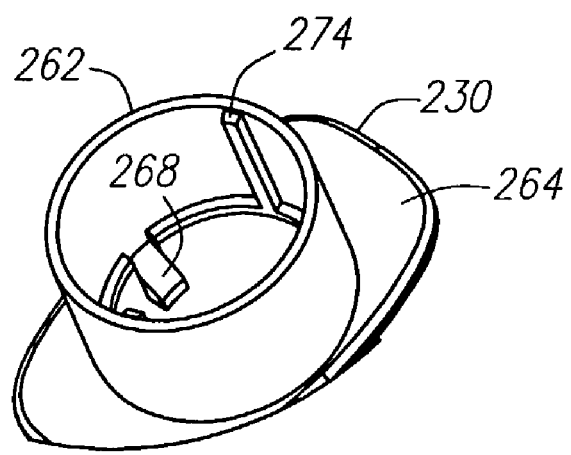
FIG. 45 is a perspective side view of the assembly of the end portion and main body of the barrel of FIGS. 35-44.
Figure 46:
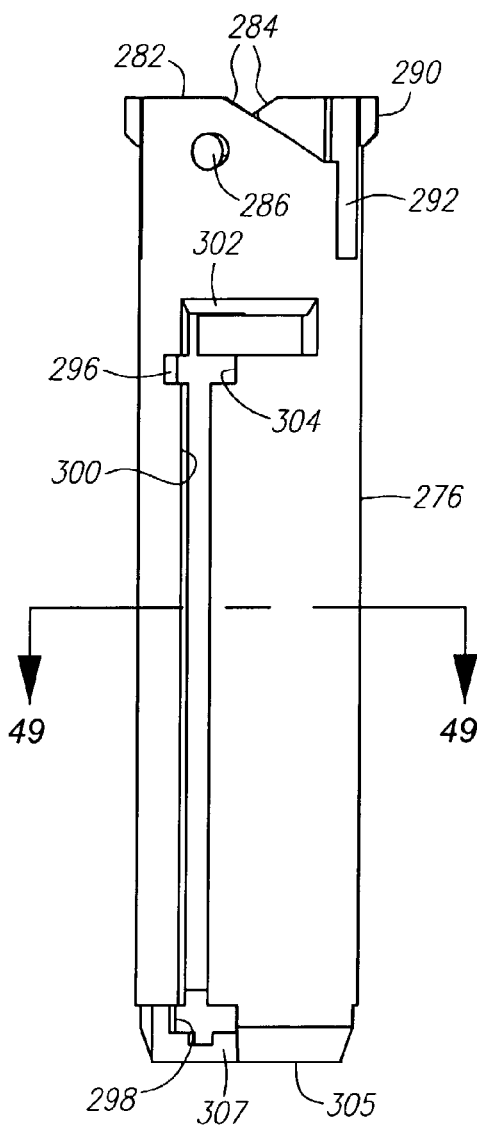
FIG. 46 is a front view of an outer plunger element of the syringe of FIG. 34.
Figure 47:
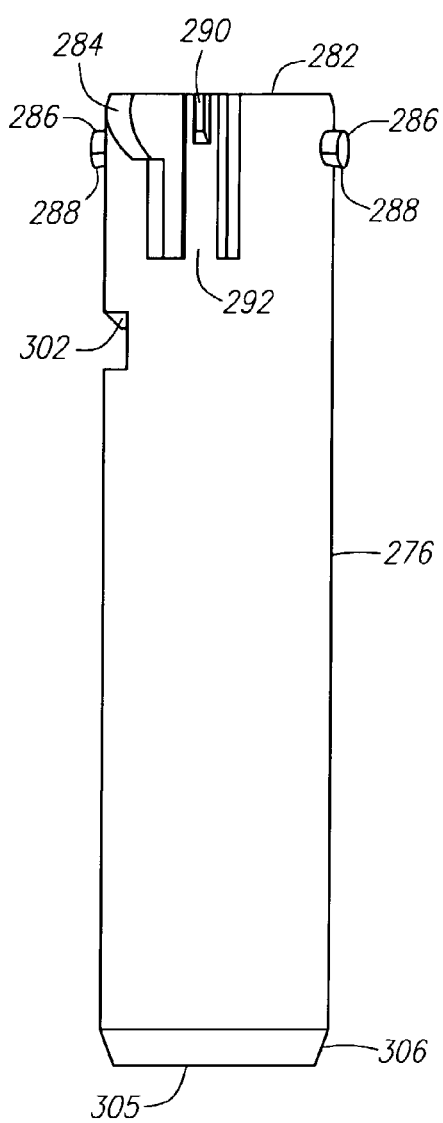
FIG. 47 is a side view of the outer plunger element of FIG. 46.
Figure 48:
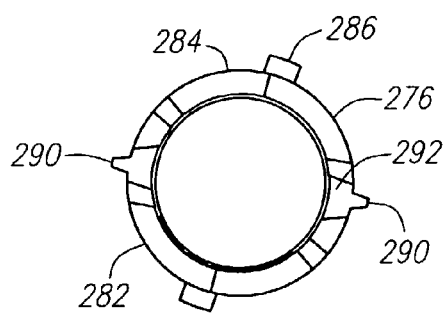
FIG. 48 is a top view of the outer plunger element of FIG. 46.
Figure 49:
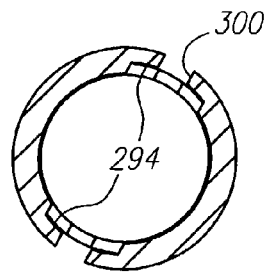
FIG. 49 is a cross-sectional plan view taken along line 49-49 of FIG. 46.
Figure 50:
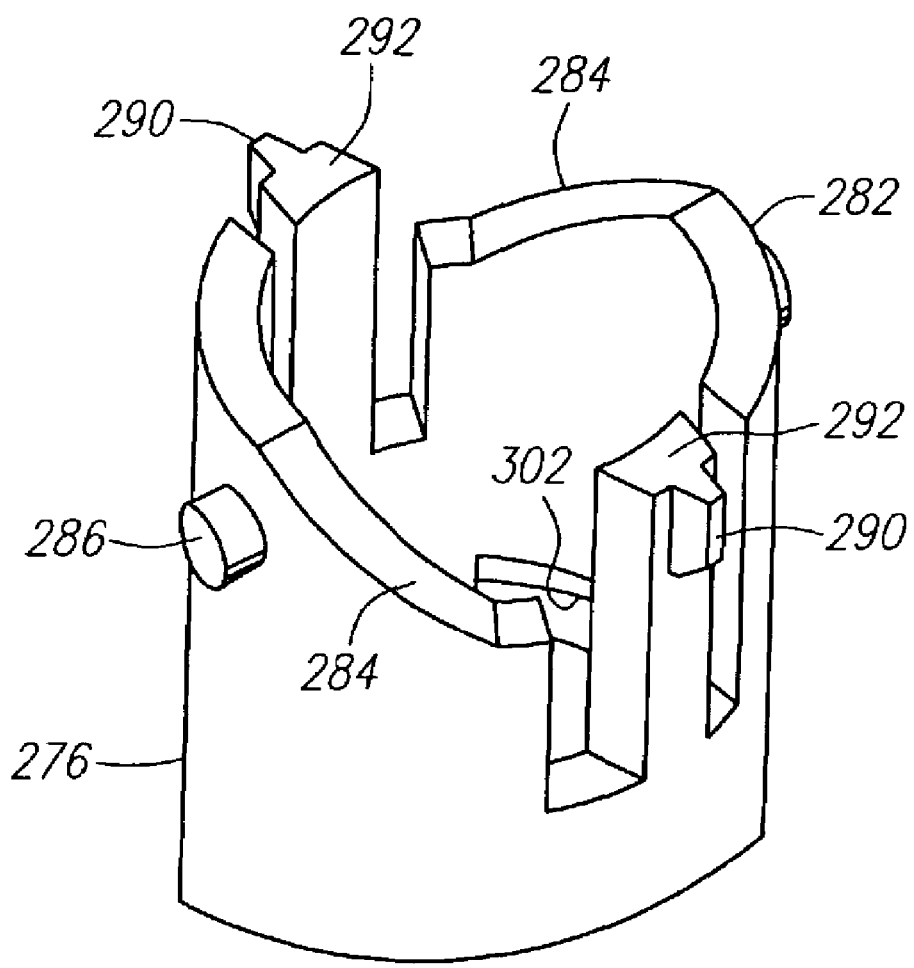
FIG. 50 is a detail perspective view of the upper end of the outer plunger element of FIG. 46.
Figure 51:
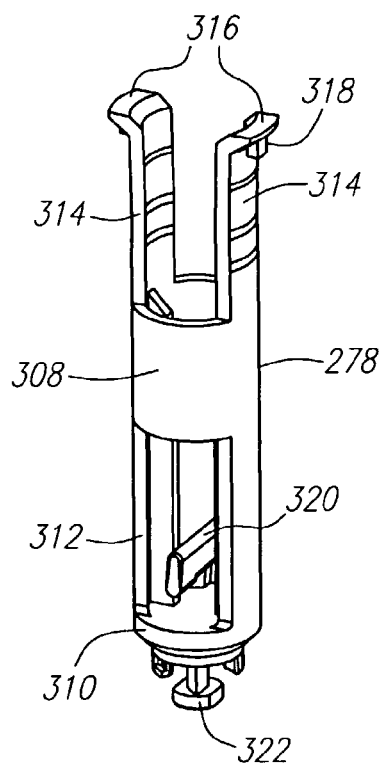
FIG. 51 is a perspective front view of an inner plunger element of the syringe of FIG. 34.
Figure 53:
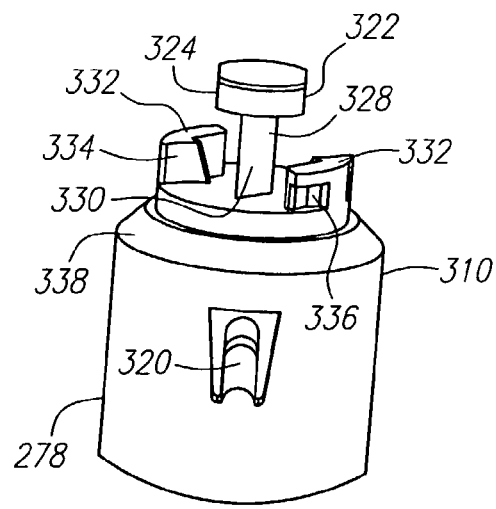
FIG. 53 is a detail view of the probe end of the inner plunger element of FIG. 51 illustrated in perspective.
Figure 52:
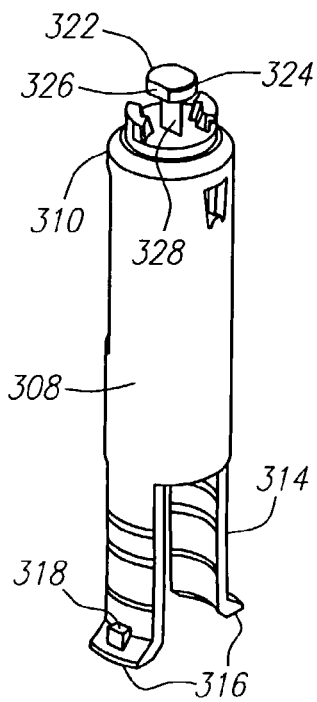
FIG. 52 is a perspective back view of the inner plunger element of FIG. 51.
Figure 54:
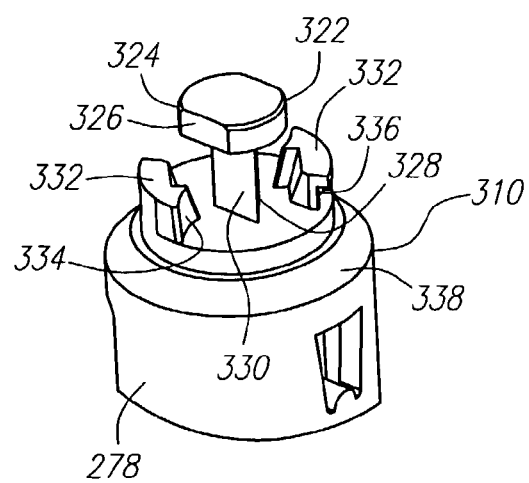
FIG. 54 is a rotated perspective view of the detail of FIG. 53.
Figure 55:
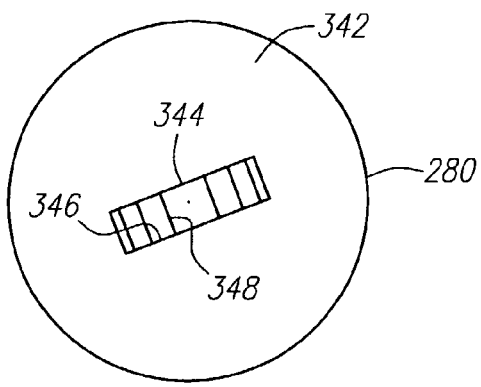
FIG. 55 is a top view of a plunger cap of the syringe of FIG. 34.
Figure 56:
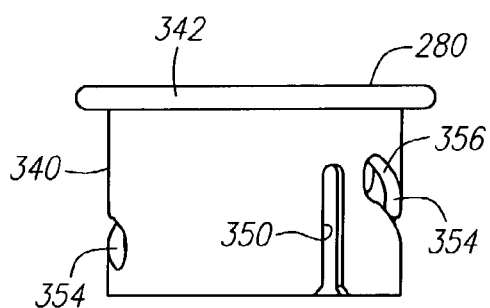
FIG. 56 is a front view of the plunger cap of FIG. 55.
Figure 57:
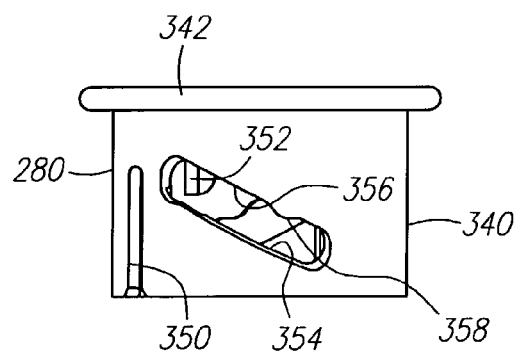
FIG. 57 is a side view of the plunger cap of FIG. 55.
Figure 58:
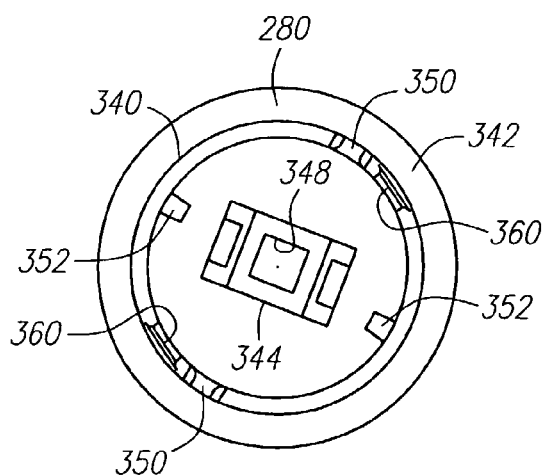
FIG. 58 is a bottom view of the plunger cap of FIG. 55.

A second embodiment of a hypodermic syringe, generally designated 220, is illustrated in FIGS. 34 through 66. In FIG. 34, an exploded assembly view is illustrated. The syringe 220 is also retractable. The several components depicted in FIG. 34 are described in greater detail with reference to the more detailed figures.

A barrel 230 is illustrated in FIGS. 35 through 45. The barrel 230 is composed of a main body 232 and an entry portion 234. The main body 232 is generally circular in cross section with a bore of varying inside diameters. At the access end 236 of the main body 232, a flange 238 extends radially outwardly from the main body 232 to define a finger grip. The side of the flange 238 facing away from the main body 232 provides a mating surface 240. Also at the access end 236, two snap sockets 242 extend downwardly from positions radially outwardly and open to the bore of the main body 232. The two snap sockets 242 are diametrically opposed. These sockets open upwardly into the mating surface 240 in order that snaps may be loaded therein.

The main body 232 is shown to be divided into three portions. The upper portion 244 receives the plunger mechanism as will be described. The middle portion 246 provides the cylindrical sealed chamber through which the sealed plunger slides in sealed engagement with the bore. A lower portion 248 forms a luer hub housing.

In the interior of the main body 232, two release elements 250 are located diametrically opposed at the junction between the upper portion 244 and the middle portion 246. As with the previous embodiment, the release elements 250 engage the rotating plunger for retraction of the lower portion into the upper portion of the plunger. The lower portion 248 extends to define the luer end 252 of the barrel 230. Diametrically opposed cavities 254 are located at the upper end of the lower portion 248. These cavities 254 define shoulders 256 upon which the luer hub can abut to resist retraction into the barrel. The lower end 252 also includes two sets of inwardly extending pins 258 and 260. As with the first embodiment, the two sets differ in height with the shorter set avoiding interference with threads on the luer hub and the difference insuring proper indexing between the luer hub and the plunger.

The entry portion 234 of the barrel 230, illustrated in FIGS. 41 through 45, includes a cylindrical body 262 having an outwardly extending flange 264 at one end. This flange 264 also defines a mating surface 266. Indexing elements in the form of snaps 268 extend downwardly from the cylindrical body 262 beyond the flange 264. The snaps 268 are configured with a thin attachment 269, a depending lock 270 and an engagement shoulder 271. This arrangement allows for the plunger to be inserted through the entry portion 234 with the snaps 268 moving outwardly to accommodate the plunger if such clearance is required. Once the plunger is positioned, the snaps 268 are moved inwardly. As the flanges 238 and 264 are brought together at the mating surfaces 240 and 266, the diametrically opposed snaps 268 extend into the snap sockets 242 on the main body 232.

A pin and socket engagement is found on the flanges 238 and 264. Pins 272 are shown on the flange 264 extending through the mating surface 266. Sockets 273 are found extending through the flange 238 from the mating surface 240. The resulting flange, split equatorially, is bonded by welding or other means. Two longitudinal guides 274 extend longitudinally on the inside of the entry portion 234 to cooperate with the plunger cap as described below.

A plunger slidably extends in the bore of the barrel 230. The plunger is an assembly including a hollow outer plunger element 276 and an inner plunger element 278. These elements 276, 278 are telescoped together. The outer plunger element 276 is illustrated in FIGS. 46 through 50. The inner plunger element 278 is illustrated in FIGS. 51 through 54. A cap 280 is retrained on the hollow outer plunger element 276. The cap 280 is illustrated in FIGS. 55 through 58.

The hollow outer plunger element 276 has a generally cylindrical body. The cap end 282 of the hollow outer plunger element 276 extends outwardly of the entry portion 234 in the barrel 230 when the device is assembled. This cap end 282 includes two cam surfaces 284 diametrically opposed on the rim of the outer plunger element 276. These cam surfaces 284 are inclined to the centerline of the cylindrical body.

The cap end 282 also includes two diametrically opposed pins 286. These pins 286 are generally cylindrical but include a barb 288 on the underside thereof to capture the cap 280. In this second embodiment, the pins 286 are not resiliently mounted to the plunder element 276 as the resilience of the cap 280 may be sufficiently flexible to accommodate assembly. Where such flexibility does not exist, resilient mountings may be employed. The pins 286 extend radially outwardly.

The cap end 282 also includes two outwardly extending guides 290 resiliently mounted on posts 292. The guides 290 are diametrically opposed and extend radially outwardly and longitudinally of the plunger element 276.

Two longitudinal indexing grooves 294 are diametrically opposed within the bore of the hollow outer plunger element 276. These grooves 294 extend longitudinally between a retraction socket 296 and an extension socket 298. The sockets 296 and 298 extend fully through the sidewall of the plunger element 276 while the grooves 294 are surface features on the inner bore. The sockets 296 and 298 extend transversely of the plunger element 276. An indexing slot 300 also extends between the retraction socket 296 and the extension socket 298. The indexing grooves 294 overlay the indexing slot 300 which extends fully through the wall of the plunger element 276. The indexing slot 300 is further illustrated to extend transversely about the wall of the plunger element 276, creating a circumferential section 302. This circumferential section 302 is raised relative to the retraction socket 296 to create a shoulder 304 at one end of the retraction socket 296.

The outer wall of the plunger element 276 at the engagement end 305 includes a bevel 306. Further, insets 307 are located about the opposed extension sockets 298 and are offset in one circumferential direction. The surfaces of the insets 307 are substantially aligned with or radially inwardly of the surface of the indexing grooves 294 found on the inner side of the plunger element 276. The insets 307 are sized to receive the release elements 250 in the bore of the barrel 230 through the rotation of the plunger.

The inner plunger element 278 includes a substantially cylindrical body 308 terminating in a circular hub 310. The cylindrical body 308 includes an access port 312. Two diametrically placed longitudinally extending arms 314 extend from one end of the cylindrical body 308 away from the circular hub 310. These arms 314 include latches 316 extending outwardly from the ends. Stops 318 are located at the latches 316. The latches 316 cooperate with the indexing grooves 294 to move between the retraction sockets 296 and the extension sockets 298 where they assume retracted and extended states. The arms 314 are not splayed out in the manner of the first embodiment. The shipping state includes the latches 316 residing in the retraction sockets 296. This position significantly unloads the arms 314 but maintains some pressure between the latches 316 and the sockets 296. Some polymeric materials are subject to creep over extended periods of loading. The reduced loading on the arms 314 by placing the latches 316 in the sockets 296 mitigates this possibility.

An attachment 320 is located on the inner side of the circular hub 310. The attachment 320 faces the attachment ends of the inner plunger element 278. The attachment 320 is a hook. The eye of a bungee anchor is able to slide onto the hook 320 to anchor the inner end of the bungee.

The seal end of the circular hub 310 includes a probe 322. The probe 322 includes a head 324 that is generally cylindrical with two diametrically positioned flat sides 326. A shaft 328 undercuts the head 324 and forms a parallelepiped in cross section, providing two parallel outwardly facing flat surfaces 330 on the shaft 328. The circular hub 310 also includes diametrically positioned cams 332 having cam surfaces 334 facing inwardly and forwardly. The cam surfaces 334 are shown to be curved for a smooth transition. The cams 332 extend axially of the circular hub 310 to define the cam surfaces 334. Additionally, undercut locking grooves 336 are found on the radially outward sides of the cams 332. Finally, the surface of the circular hub 310 about the probe 322 and cams 332 includes an annular truncated conical sealing surface 338.

A plunger cap 280 is positionable on the cap end 282 of the outer plunger element 276 as illustrated in FIG. 34. The cap 280 includes an annular body 340 and a thumb button 342 extending across one end of the annular body 340. The thumb button 342 defines an attachment 344 centered axially of the annular body 340. An attachment slot 346 is arranged in the thumb button 342 with a hole 348 extending to the attachment slot 346 to receive a T-head on a bungee.

The annular body 340 includes two longitudinal slots 350 diametrically positioned and extending to the free end of the annular body 340. These slots 350 engage the longitudinal guides 274 in the barrel 230. The slots 350 also engage the guides 290 as well. The engagement of the slots 350 with the guides 290 occurs during the conventional actuation of the plunger. The longitudinal guides 270 engage the longitudinal slots 350 only once the plunger is advanced substantially fully into the barrel 230.

The annular body 340 further includes cam drivers 352 diametrically placed on the inner surface of the annular body 340. These cam drivers 352 engage the cam surfaces 284 on the cap end 282 of the outer plunger element 276 with the cap 280 in place on the plunger.

Inclined slots 354 are also diametrically positioned on the annular body 340 and extend therethrough. The inclined slots 354 are sized to receive the radially extending pins 286 near the cap end 282 of the outer plunger element 276. One side 356 of each of the inclined slots 354, which faces toward the luer end 252 of the barrel 230 when the plunger is positioned in the barrel, includes a resistance lock 358. The components of the syringe, with the exception of the needle, are preferably of a polymeric material. Consequently, the material is able to flex in appropriate configurations. The resistance lock 358 is a rounded bump which, in this embodiment, is not structurally relieved. The size of the pins 286 and of the bumps 358 are determined to provide an appropriate amount of resistance to define an easily perceived separation between the conventional plunger movement and the rotation of the plunger in the barrel. The pins 286 including slight barbs 288 somewhat interlock with the inclined slots 354. Lead-in grooves 360 on the inner side of the annular body 340 extending to the inclined slots 354 assist in the assembly of the cap 280 on the outer plunger element 276.

Figure 59:
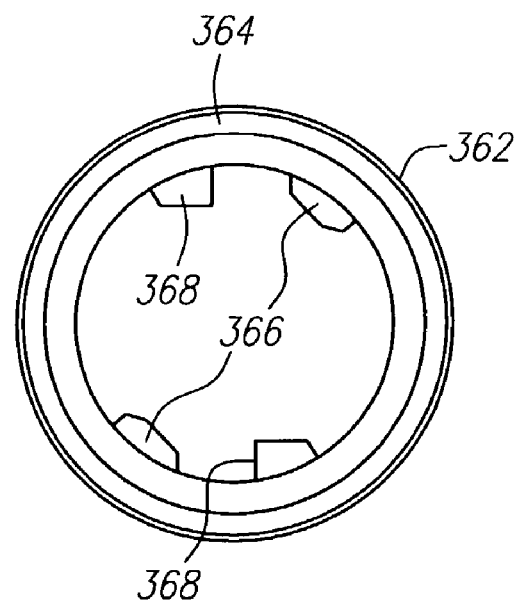
FIG. 59 is a top view of the seal stop of the syringe of FIG. 34.
Figure 60:
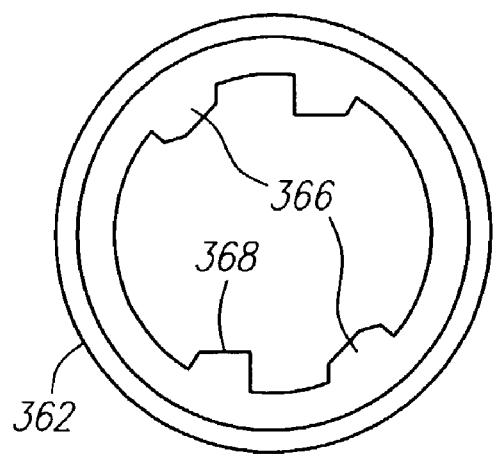
FIG. 60 is a bottom view of the seal stop of FIG. 59.
Figure 61:
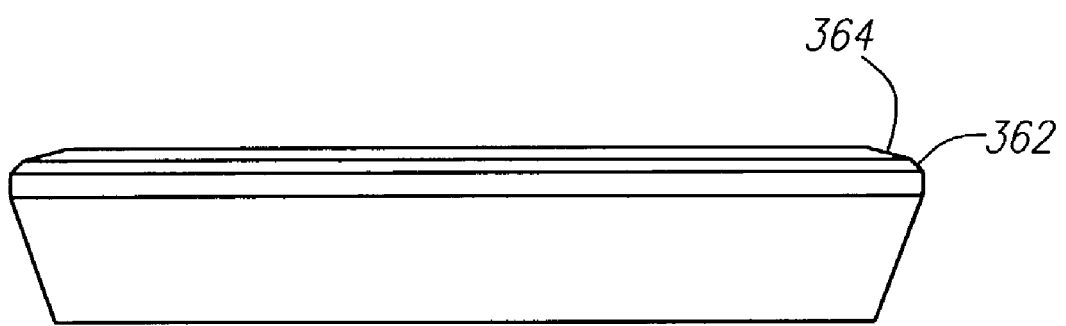
FIG. 61 is a side view of the seal stop of FIG. 59.

A seal stop 362, illustrated in FIGS. 59 through 61, is mounted to the leading side of the circular hub 310 of the plunger. The seal stop 362 is releasable from the circular hub 310 with rotation of the stop 362 relative to the hub 310. The seal stop 362 includes an annular truncated conical surface 364 which cooperates with the surface 338 of the circular hub 310 to define an annular pinch. The seal stop 362 forms a ring with an inner cylindrical surface positionable about the cams 332 on the circular hub 310. Two inwardly extending mounting lugs 366 are retained by the undercut locking grooves 336. Stops 368 are appropriately spaced angularly from the mounting lugs 366. The conical surfaces 364 and 338 defining the pinch are able to receive an annular plunger seal 370 in radial expansion within the pinch. The mechanism is sized to force the seal 370 outwardly to seal with the barrel 230.

A luer hub 372 is illustrated in detail in FIGS. 62 through 65. The luer hub 372 is located in the lower portion 248 of the barrel 230. It is axially and rotationally fixed but can be released to axially slide in the barrel 230 from the luer end 252 toward the access end 236. The hub 372 includes a generally cylindrical body 374 having a passage 376 extending axially therethrough. Notches 378, 380 receive the pins 258, 260 which both prevent the luer hub 372 from rotating within the lower portion 248 of the barrel 230. The pins 258, 260 also prevent the luer hub 372 from moving axially from the luer end 252 of the syringe. Internal threads 382 within the skirt 384 of the luer hub 372 meet ISO-594-2 for attachment of a needle assembly thereto. An annular groove 386 receives a seal 388, typically an O-ring. This seal 388 seals the bottom end of the syringe by sealing against the lower portion 248 of the barrel 230.

Figure 62:
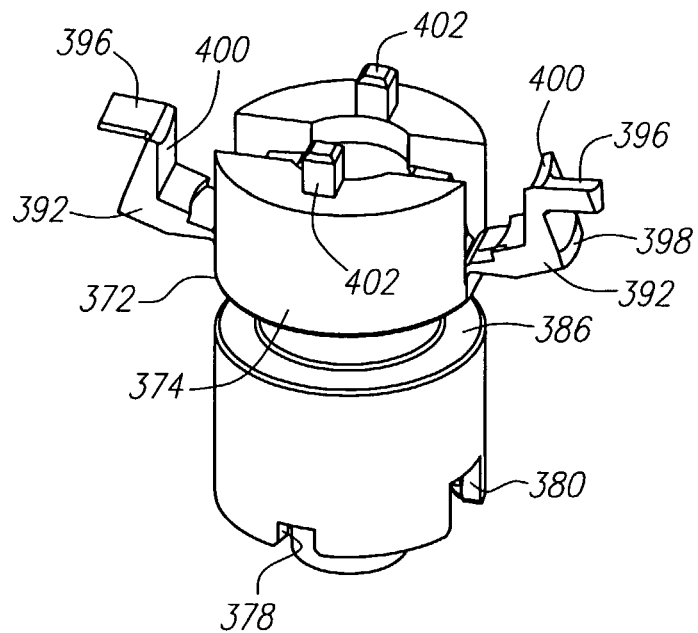
FIG. 62 is a perspective view of a luer hub of the syringe of FIG. 34 in the mold state.
Figure 63:
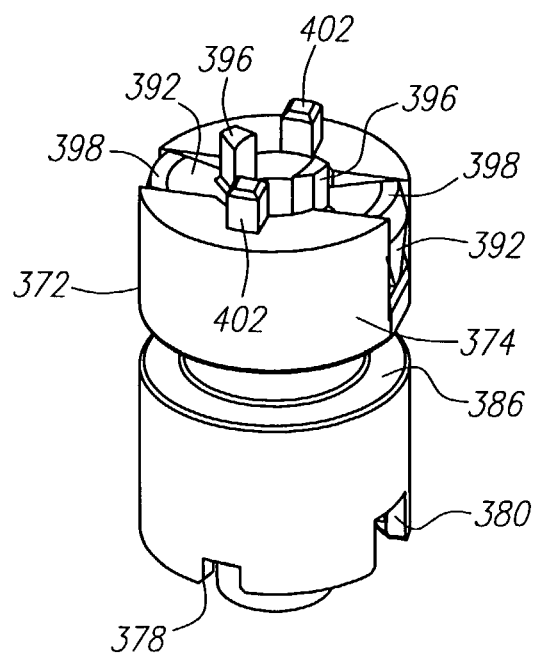
FIG. 63 is a perspective view of the luer hub of FIG. 62 in the assembled state.
Figure 64:
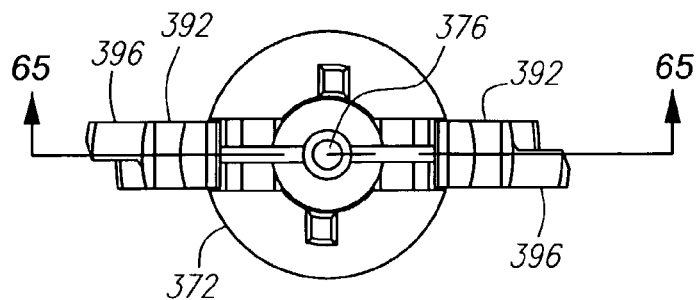
FIG. 64 is a top view of the luer hub as illustrated in FIG. 62.
Figure 65:
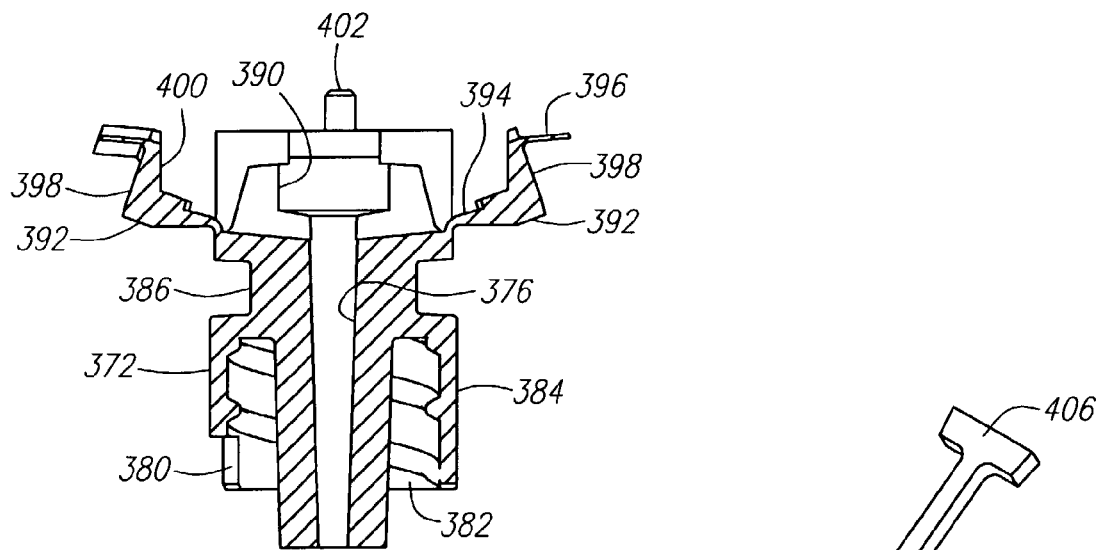
FIG. 65 is a cross-sectional view of the luer hub taken along line 65-65 of FIG. 64.
Figure 66:
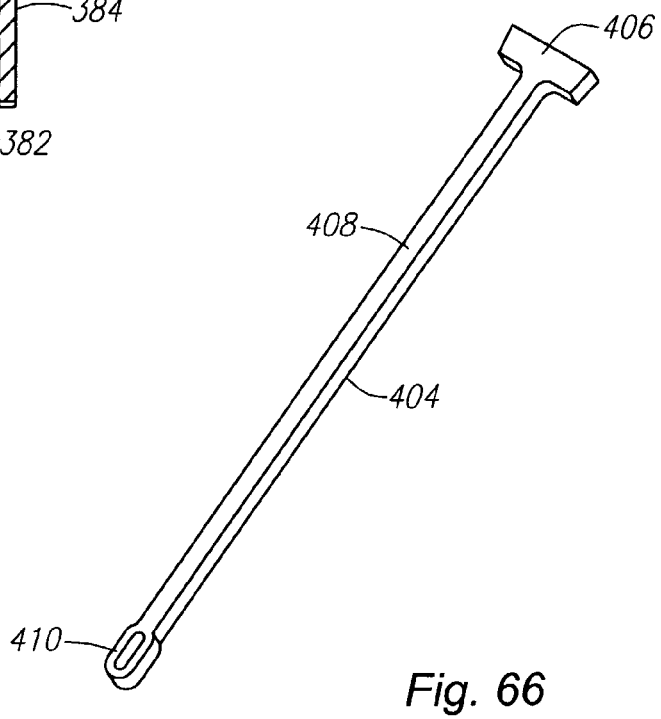
FIG. 66 is a perspective view of the resilient tension element of the syringe of FIG. 34.

The engagement end of the luer hub 372 includes a concentrically arranged recess 390 facing the plunger. The recess is arranged and positioned to accept the head 324 of the probe 322. With the head 324 contacting the bottom of the recess 390, the plunger is substantially fully extended into the barrel 230. Two elements 392 are diametrically placed about the recess 390 on the end of the luer hub 372. These elements 392 are resiliently mounted to the luer hub 372 by living hinges 394 to pivot radially of the luer hub 372. In FIG. 62, these elements 392 are shown in the orientation in which they are molded. In FIG. 63, the elements 392 have been pivoted radially inwardly. The elements 392 each include a cam follower 396 which extends toward the plunger for engagement with the cam surfaces 334. Locking surfaces 398 are also mounted to the elements 392 and extend radially outwardly to axially engage the shoulders 256 of the barrel 230. Latches 400 extend radially toward and above the recess 390 to angularly and axially engage the probe 322 by extending into the undercut shaft 328 to the flat surfaces 330. Engagements 402 extend upwardly from the luer hub 372 toward the plunger. These engagements 402 extend to the seal stop 362 to interfere with rotation of the stops 368.

A bungee 404 is illustrated as cut from flat stock. The bungee includes a T-head 406, a shaft 408 square in cross section and an eye 410.

For assembly, the luer O-ring 388 is placed in the groove 386 of the luer hub 372, which is then positioned in the lower portion 248 of the barrel 230 with the notches 378 and 380 positioned on the pins 258 and 260. The elements 392 must be rotated inwardly of the living hinges 394 to achieve insertion and placement within the barrel 230. Because of the natural resilience of the living hinges 394, the locking surfaces 398 extend outwardly beyond the periphery of the luer hub 372 to engage the shoulders 256 of the cavities 254 on the lower portion 248 of the barrel 230. In this position, the luer hub is fixed from either rotational movement or axial movement relative to the barrel 230.

The plunger is assembled by locking the seal stop 362 to the undercut locking grooves 338 and placing a tensioned plunger seal 370 in the pinch created. The hollow outer plunger element 276 and the inner plunger element 278 are then assembled with the latches 316 forced inwardly to be extended into the hollow outer plunger element 276 and engage the grooves 294. The latches are then slid upwardly to engage the retraction sockets 296.

The T-head 406 of the bungee 404 is distorted and forced through the hole 348 and then drawn flush against the attachment slot 346. The shaft 408 of the bungee is then let down into the bore of the hollow outer plunger element 276 and between the arms 314. The access port 312 provides access to reach the eye 410 of the bungee 404 and engage the attachment 320.

The plunger cap 280 is then associated with the upper end of the outer plunger element 276. The pins 286 are positioned in lead-in grooves 360 and forced into the inclined slots 354. Once in the slots 354, the pins 286 are fully radially extended such that the barbs 288 engage the annular body 340. The cam drivers 352 then engage the cam surfaces 284 of the outer plunger element 276.

With the assembly of the annular body 340 about the cap end 282 of the outer plunger element 276, the guides 290 reside in the longitudinal slots 350. Thus, the cap 280 cannot rotate relative to the outer plunger element 276. The pins 286 are arranged in the inclined slots 354 at the ends of the slots captured by the resistance locks 358. The plunger assembly thus configured is positioned through the entry portion 234 which is yet to be assembled with the main body 232 of the barrel 230. The entry portion, displaced from the main body 232, allows the snaps 268 to move outwardly as the plunger assembly is being inserted through the entry portion 234. The snaps 268 are then pushed inwardly to engage the indexing slots 300. The assembled entry portion 234 with the plunger assembly is brought together with the main body 232. In doing so, the snaps 268 are positioned in the snap sockets 242.

The pins 272 engage the sockets 273 and the equatorial split in the finger grip between the flanges 238 and 264 is bonded or welded together.

A needle assembly may be or has been attached to the internal threads 382 of the luer hub 372 and a cap is placed over the needle. In this initial assembly for packing and storage, the plunger is contracted and advanced substantially fully into the barrel 230.

For use, the plunger cap 280 is gripped along with the barrel 230. The cap 280 is drawn outwardly from the barrel 230. As the pins 286 are engaged with the inclined slots 354, the plunger assembly is drawn outwardly from the barrel 230 as well. The snaps 268 interfere with movement of the latches 316 on the arms 314 with the outer plunger element 276. As the plunger cap 280 is pulled, the latches 316 are forced by beveled undersides to exit the retraction slots 296 and ride within the grooves 294 as the outer plunger element 276 is drawn outwardly of the barrel 320 relative to the snaps 268. This tensions the bungee 404 and ultimately allows the latches 316 to snap into locking engagement with the extension lots 298. The plunger assembly has, through this action, gone from a shipping state to an extended state with the bungee 404 now in tension. Excessive withdrawal of the plunger assembly from the barrel 230 is prevented by the snaps 268 continuing to ride on the latches 316.

With the syringe thus cocked, the plunger is advanced in the barrel 230 toward the luer end of the barrel. The plunger remains in the extended state during this operation. The cap 280 is not pressed into actuating compression toward the outer plunger element 276 at this point.

The cap may then be removed and the needle injected into a bottle of fluid to be hypodermically injected into a patient. The plunger is drawn back for the proper dosage. Again, the barrel 230 is held and the plunger cap 282 is drawn away from the barrel. The pins 286 draw the plunger assembly with the plunger cap 280. The injection is accomplished in a normal manner and the needle removed from the subject receiving the injection.

Once the plunger is again substantially fully inserted into the barrel, the fluid having been injected into the subject, the cap 280 is forced toward the barrel 230. At this point, the snaps 268 are aligned with the circumferential sections 302 of the longitudinal indexing slots 300. With this alignment, the plunger can rotate within the barrel 230 without interference from the snaps 268. Further, the longitudinal guides 274 enter the longitudinal slots 350 on the annular body 340 of the plunger cap 280. The guides 290 are forced out of the longitudinal slots 350 by the longitudinal guides 274 with movement of the plunger cap 280 toward the barrel 230. The guides 290 are forced from the slots 350. Consequently, the plunger cap 280 cannot rotate relative to the barrel 230 but now can rotate relative to the outer plunger element 276.

Further application of pressure to the thumb button 342 causes the cam drivers 352 to engage the cam surfaces 284 of the outer plunger element 276. The inclined slots 354 bear against the pins 286. With the cap 280 bearing against the outer plunger element 276 on inclined surfaces, the plunger assembly begins to rotate relative to the cap. Again, the cap 280 is now affixed from rotation relative to the barrel 230. The resistance locks 358, configured to allow tactile differentiation between an injection stroke and a needle retracting stroke, are overcome by pressure on the thumb button.

At the point that the plunger cap 280 is able to initiate rotation of the plunger assembly, the head 324 of the probe 322 on the circular hub 310 is located in the recess 390 of the luer hub 372 with that contact preventing additional advancement of the plunger within the barrel 230. As the plunger rotates through further advancement of the plunger cap 280, the probe 322, the cams 332 and the seal stop 362 rotate. The cam surfaces 334 are oriented to move the cam followers 396 inwardly. Therefore, as the plunger rotates, the cams 332 move the locking surfaces 398 and the latches 400 inwardly. The pins 258 and 260 retain the luer hub 372 from rotating under the influence of the cams 332. The locking surfaces 398 are drawn in this way from the shoulders 356. The latches 400 extend to engage the head 324 of the probe 322 by extending into the undercut shaft 328. With this motion, the luer hub 372 is released to move axially and is engaged with the plunger assembly.

The engagements 402 simultaneously interfere with the rotation of the seal stop 362 by contacting the stops 368. As the plunger assembly continues to rotate, the mounting lugs 366 are rotated from engagement with the undercut locking grooves 336 on the cams 332. Once unlocked, the annular plunger seal 370 is released to contract away from the barrel 230. Thus, the seal does not generate resistance against motion of the inner plunger element 378.

With the annular plunger seal 370 released, the luer hub 372 capturing the head 324 of the probe 322 and the locking surfaces 398 released from the shoulders 256 of the barrel 230, the needle assembly is prepared to be retracted. Under the influence of the plunger cap 280, continued rotation of the plunger brings the latches 316 into engagement with the release elements 250 in the bore of the barrel 230. The latches 316 are driven inwardly until they release from the extension sockets 298. The bungee 404 then is able to draw the inner plunger element 278 along with the captured luer hub 372 upwardly into the barrel 230. As the bungee 404 is at its most stress with the luer hub still in the lower portion 248 of the barrel 230, the luer hub 272 can be drawn into the larger middle portion 246 of the barrel 230 against the resistance of the O-ring 388 without the need to relieve it from the bore of the barrel. The lower portion 248 of the barrel 230 may also be slightly conical in shape to allow greater relief as the seal 388 moves upwardly.

The head 324 on the probe 322 is arranged such that it is displaced from the latches 400 with the probe 322 fully seated in the recess 390. As the luer O-ring seal 388 remains about the luer hub 372 as the plunger begins to retract, the plunger will first start to draw a vacuum between the circular hub 310 and the luer hub 372 prior to the head 324 engaging the latches 400. This increase in volume behind the luer hub 372 draws liquid from the needle assembly to avoid splash as the needle is then withdrawn.

The placement of the snaps 268 in the circumferential section 302 of the indexing slot 300 prevents retraction of the outer plunger element 276 and all other components from the barrel 230. The snaps 268 are also not able to reenter the longitudinal portions of the slots 300 because of the latches 316 located in the retraction sockets 296 following telescoping together of the plunger elements 276 and 278.

Thus, an improved hypodermic syringe and a process for needle retraction are disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A retractable syringe comprising
a barrel including a bore, a first end and a second end;
a luer hub at the first end of the barrel releasable to move longitudinally of the barrel;
a plunger slidably positioned within the barrel and rotatable within the barrel with substantially full extension toward the first end of the barrel to release the luer hub;
a cap at one end of the plunger extending from the barrel and including an annular body, a cam driver fixed to the cap and an inclined slot in the annular body, the plunger including a cam surface at the one end of the plunger inclined to the centerline of the bore with the plunger in the barrel and engageable with the cam driver and a pin extending substantially radially of the plunger adjacent the one end of the plunger and engageable with the inclined slot.

2. The retractable syringe of claim 1, there being multiple said cam surfaces and an equal number of said cam drivers engageable with the said cam surfaces, respectively.

3. The retractable syringe of claim 2, the said cam drivers being equiangularly spaced on the annular body.

4. The retractable syringe of claim 3, there being two said cam drivers diametrically located on the inner side of the annular body.

5. The retractable syringe of claim 1, the inclined slot having a first side inclined facing toward the barrel and a resistance lock at the first side and extending into the slot.

6. The retractable syringe of claim 5, the resistance lock being a rounded bump in the first side, the annular body being structurally relieved behind the rounded bump.

7. The retractable syringe of claim 6, the pin being cylindrical.

8. The retractable syringe of claim 7, the pin including a barb on the distal end thereof.

9. The retractable syringe of claim 6, the pin extending radially outwardly from the plunger.

10. The retractable syringe of claim 9, the pin being resiliently mounted to the plunger.

11. The retractable syringe of claim 1, one of the barrel and the annular body of the cap further including a longitudinal slot and the other of the barrel and the annular body of the cap including a longitudinal guide engageable with the longitudinal slot to prevent rotation of the cap relative to the barrel with the cap in the barrel.

12. The retractable syringe of claim 1, the plunger further including a hollow outer plunger element receiving the cap, the cap including a first attachment facing into the hollow outer plunger element, a hollow inner plunger element telescoping together with the hollow outer plunger element and having a second attachment facing the first attachment and located axially in the hollow inner plunger element near the end most distant from the cap, a resilient tension element fixed to the first attachment and the second attachment and being just substantially relaxed with the outer plunger element and the inner plunger element telescoped together and a releasable engagement between the hollow outer plunger element and the hollow inner plunger element engageable with the hollow outer plunger element and the hollow inner plunger element telescoped to an extended position and releaseable with rotation of the plunger.

13. A retractable syringe comprising
a barrel including a bore, a first end and a second end;
a luer hub at the first end of the barrel releasable to move longitudinally of the barrel;
a plunger slidably positioned within the barrel and rotatable within the barrel with substantially full extension toward the first end of the barrel;
a cap at one end of the plunger extending from the barrel and including an annular body and an inclined slot in the annular body having a first side inclined facing toward the barrel and a resistance lock at the first side and extending into the slot, the plunger including a pin extending substantially radially of the plunger adjacent the one end of the plunger and engageable with the inclined slot.

14. The retractable syringe of claim 13, the resistance lock being a rounded bump in the first side, the annular body being structurally relieved behind the rounded bump.

15. The retractable syringe of claim 14, the pin being cylindrical.

16. The retractable syringe of claim 15, the pin including a barb on the distal end thereof.

17. The retractable syringe of claim 14, the pin extending radially outwardly from the plunger.

18. The retractable syringe of claim 17, the pin being resiliently mounted to the plunger.

19. The retractable syringe of claim 13, the plunger further including a hollow outer plunger element receiving the cap, the cap including a first attachment facing into the hollow outer plunger element, a hollow inner plunger element telescoping together with the hollow outer plunger element and having a second attachment facing the first attachment and located axially in the hollow inner plunger element near the end most distant from the cap, a resilient tension element fixed to the first attachment and the second attachment and being just substantially relaxed with the outer plunger element and the inner plunger element telescoped together and a releasable engagement between the hollow outer plunger element and the hollow inner plunger element engageable with the hollow outer plunger element and the hollow inner plunger element telescoped to an extended position and releaseable with rotation of the plunger.

20. A retractable syringe comprising a barrel including a bore, a first end and a second end;

a luer hub at the first end of the barrel releasable to move longitudinally of the barrel;

a plunger slidably positioned within the barrel and rotatable within the barrel with substantially full extension toward the first end of the barrel;

a cap at one end of the plunger extending from the barrel and including an annular body, cam drivers fixed to the cap and inclined slots in the annular body, each inclined slot having a first side inclined facing toward the barrel and a resistance lock at the first side and extending into the slot, the plunger including cam surfaces at the one end of the plunger inclined to the centerline of the bore with the plunger in the barrel and engageable with the cam drivers, respectively, and pins extending substantially radially of the plunger adjacent the one end of the plunger and engageable with the inclined slots, respectively, the cam drivers being equiangularly spaced on the annular body and the pins being equiangularly spaced on the plunger.

21. The retractable syringe of claim 20, the resistance locks being rounded bumps in the first sides, the annular body having relief behind the rounded bumps.

22. The retractable syringe of claim 21, the pin being cylindrical.

23. The retractable syringe of claim 22, the pin including a bar on the distal end thereof.

24. The retractable syringe of claim 23, the pin being resiliently mounted to the plunger.

25. The retractable syringe of claim 20, the plunger further including a hollow outer plunger element receiving the cap, the cap including a first attachment facing into the hollow outer plunger element, a hollow inner plunger element telescoping together with the hollow outer plunger element and having a second attachment facing the first attachment and located axially in the hollow inner plunger element near the end most distant from the cap, a resilient tension element fixed to the first attachment and the second attachment and being just substantially relaxed with the outer plunger element and the inner plunger element telescoped together and a releasable engagement between the hollow outer plunger element and the hollow inner plunger element engageable with the hollow outer plunger element and the hollow inner plunger element telescoped to an extended position and releaseable with rotation of the plunger.

* * * * *